US012734035B2

(12) United States Patent
Keränen

(10) Patent No.: US 12,734,035 B2
(45) Date of Patent: Sep. 15, 2026

(54) ANNULOPLASTY DEVICE

(71) Applicant: HVR Cardio Oy, Espoo (FI)

(72) Inventor: Olli Keränen, Bjärred (SE)

( * ) Notice: Subject to any disclaimer, the term of this patent is extended or adjusted under 35 U.S.C. 154(b) by 828 days.

(21) Appl. No.: 18/015,731

(22) PCT Filed: Jan. 13, 2021

(86) PCT No.: PCT/EP2021/050600
§ 371 (c)(1),
(2) Date: Jan. 12, 2023

(87) PCT Pub. No.: WO2022/012782
PCT Pub. Date: Jan. 20, 2022

(65) Prior Publication Data

US 2023/0255771 A1 Aug. 17, 2023

(30) Foreign Application Priority Data

Jul. 13, 2020 (WO) ................. PCT/EP2020/069804
Nov. 13, 2020 (EP) .................................... 20207665

(51) Int. Cl.
*A61F 2/24* (2006.01)
*A61B 17/00* (2006.01)
*A61F 2/848* (2013.01)

(52) U.S. Cl.
CPC .. *A61F 2/2445* (2013.01); *A61B 2017/00243* (2013.01); *A61F 2/2448* (2013.01); *A61F 2002/8483* (2013.01); *A61F 2210/0014* (2013.01); *A61F 2220/0016* (2013.01); *A61F 2230/0091* (2013.01)

(58) Field of Classification Search
CPC ........ A61F 2/2445–2448; A61F 2/2409; A61F 2230/0091
See application file for complete search history.

(56) References Cited

U.S. PATENT DOCUMENTS

2014/0379074 A1* 12/2014 Spence ................. A61F 2/2466 623/2.11
2018/0177594 A1* 6/2018 Patel ..................... A61F 2/2418
2019/0350707 A1* 11/2019 Zerkowski ............ A61F 2/2445

* cited by examiner

*Primary Examiner* — Rebecca S Preston
(74) *Attorney, Agent, or Firm* — Patent Grove AB; Tomas Friend

(57) ABSTRACT

An annuloplasty device is disclosed comprising first and second support rings having a coiled configuration, and respective first and second retention units, the first support ring transitions to the second support ring over a transition section, the transition section is adapted to be arranged at a commissure of the heart valve leaflets, a first posterior bow of the first support ring and a second posterior bow of the second support ring extend in respective first and second coil planes being essentially perpendicular to the central axis, the transition section bends at least partly along the central axis so that the first coil plane is separated a distance from the second coil plane along the central axis at the transition section.

20 Claims, 17 Drawing Sheets

ANNULOPLASTY DEVICE

FIELD OF THE INVENTION

This invention pertains in general to the field of cardiac valve repair. More particularly the invention relates to an annuloplasty device, such as an annuloplasty ring or helix, for positioning at the heart valve annulus and a method of repairing a defective heart valve.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. The annuloplasty ring is typically implanted around the annulus of the heart valve.

A problem with prior art annuloplasty implants is to achieve correct positioning at the heart valve and fixate the implant in the correct position. Suturing devices for annuloplasty implants have disadvantages that makes it difficult to suture in the correct position, thereby resulting insufficient suturing strength, and also in a very time-consuming procedure, which increases the risks for the patient. Furthermore, suturing devices are often not sufficiently compact for catheter based procedures. The use of clips for positioning annuloplasty implants is also associated with challenges, in particular when implanting helix rings that are to be positioned on either side of a heart valve. Insufficient fixation of such implant lead to traumatic effects since the fixation structure must ensure the correct position of the device over time. A further problem in the prior art is thus also to achieve a reliable fixation at the annulus of the heart valve. An annuloplasty implant is intended to function for years and years, so it is critical with long term stability in this regard.

The above problems may have dire consequences for the patient and the health care system. Patient risk is increased.

Hence, an improved annuloplasty implant or device would be advantageous and in particular allowing for avoiding more of the above mentioned problems and compromises, and in particular ensuring secure fixation of the annuloplasty device, during the implantation phase, and for long-term functioning, in addition to a less complex procedure, and increased patient safety. A related method would also be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect an annuloplasty device is provided comprising first and second support rings having a coiled configuration in which the first and second support rings are arranged as a coil around a central axis, the central axis extending in an axial direction from the second support ring to the first support ring, wherein the first and second support rings are configured to be arranged on opposite sides of native heart valve leaflets of a heart valve, wherein the first support ring is adapted to be arranged on an atrial side of said heart valve, and the second support ring is adapted to be arranged on a ventricular side of the heart valve, wherein the first support ring comprises a first posterior bow and a first anterior portion, the second support ring comprises a second posterior bow and a second anterior portion, the first and second posterior bows are adapted to conform to a posterior aspect of said heart valve, and the first and second anterior portions are adapted to conform to an anterior aspect of said heart valve, wherein the first support ring transitions to the second support ring over a transition section, wherein the transition section is adapted to be arranged at a commissure of the heart valve leaflets, wherein the first posterior bow of the first support ring and the second posterior bow of the second support ring extend in respective first and second coil planes being essentially perpendicular to the central axis, and wherein the transition section bends at least partly along the central axis so that the first coil plane is separated a distance from the second coil plane along the central axis at the transition section.

According to a second aspect an annuloplasty device is provided comprising first and second support rings having a coiled configuration in which the first and second support rings are arranged as a coil around a central axis, the central axis extending in an axial direction from the second support ring to the first support ring, wherein the first and second support rings are configured to be arranged on opposite sides of native heart valve leaflets of a heart valve, wherein the first support ring is adapted to be arranged on an atrial side of said heart valve, and the second support ring is adapted to be arranged on a ventricular side of the heart valve, wherein the first support ring comprises a first posterior bow and a first anterior portion, the second support ring comprises a second posterior bow and a second anterior portion, the first and second posterior bows are adapted to conform to a posterior aspect of said heart valve, and the first and second anterior portions are adapted to conform to an anterior aspect of said heart valve, wherein a tilted section of the first anterior portion raise above the first posterior bow in the axial direction.

According to a third aspect an annuloplasty device is provided comprising first and second support rings having a coiled configuration in which the first and second support rings are arranged as a coil around a central axis, the central axis extending in an axial direction from the second support ring to the first support ring, wherein the first and second support rings are configured to be arranged on opposite sides of native heart valve leaflets of a heart valve, wherein the first support ring is adapted to be arranged on an atrial side of said heart valve, and the second support ring is adapted to be arranged on a ventricular side of the heart valve, wherein the first support ring comprises a first posterior bow and a first anterior portion, the second support ring comprises a second posterior bow and a second anterior portion, the first and second posterior bows are adapted to conform to a posterior aspect of said heart valve, and the first and second anterior portions are adapted to conform to an anterior aspect of said heart valve, wherein the second anterior portion comprises an inverted section extending in parallel with the first and second coil planes, wherein the inverted section and the second posterior bow extend on opposite sides of the first posterior bow with respect to the direction of the central axis.

According to a fourth aspect a method of repairing a defective heart valve is provided, comprising positioning a second support ring of an annuloplasty device on a ventricular side of the heart valve, and positioning a first support ring of the annuloplasty device on an atrial side of the heart valve, the first and second support rings are arranged as a coil around a central axis on opposite sides of native heart valve leaflets of the heart valve. The first and second support rings are positioned so that the first support ring transitions to the second support ring over a transition section positioned at a commissure of the heart valve leaflets. The first and second support rings extend in respective first and second coil planes being essentially perpendicular to the central axis. The transition section bends at least partly along the central axis so that the first coil plane is separated a distance from the second coil plane along the central axis at the transition section.

Further examples of the invention are defined in the dependent claims, wherein features for the first aspect may be implemented for the second and subsequent aspects and vice versa.

Some examples of the disclosure provide for a facilitated positioning of an annuloplasty device at a heart valve.

Some examples of the disclosure provide for a facilitated fixation of an annuloplasty device at a heart valve.

Some examples of the disclosure provide for a less time-consuming fixation of an annuloplasty to a target site.

Some examples of the disclosure provide for securing long-term functioning and position of an annuloplasty device.

Some examples of the disclosure provide for a reduced risk of damaging the anatomy of the heart such as the annulus or the valve leaflets.

Some examples of the disclosure provide for a more secure implantation of an annuloplasty device in narrow anatomies.

Some examples of the disclosure provide for an annuloplasty device with improved accommodation to the anatomy of a heart valve.

Some examples of the disclosure provide for an annuloplasty device with an increased retention force at the heart valve.

It should be emphasized that the term “comprises/comprising” when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
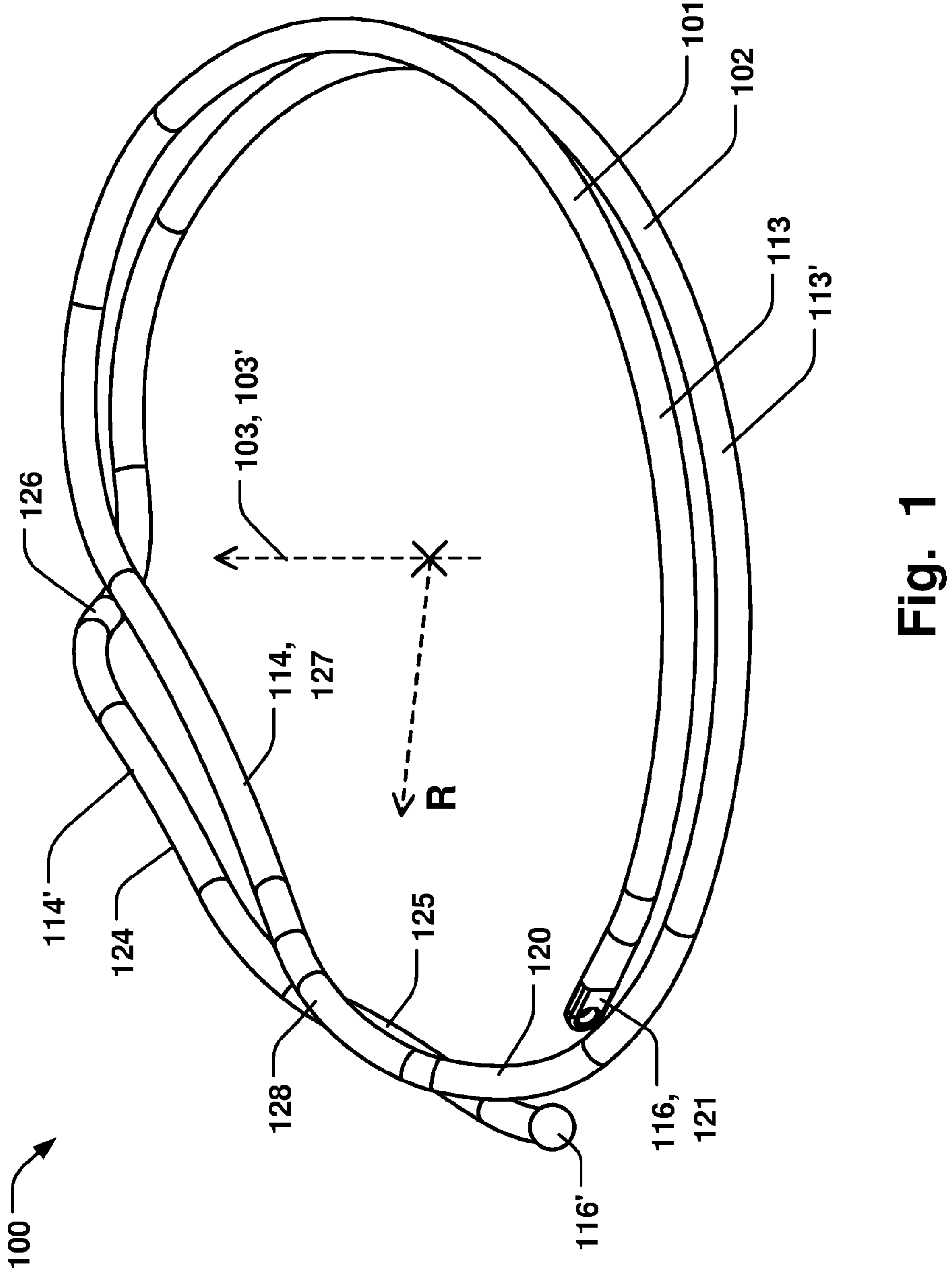
FIG. 1 is a schematic illustration of an annuloplasty device, in a perspective view, according to an example.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 10A:
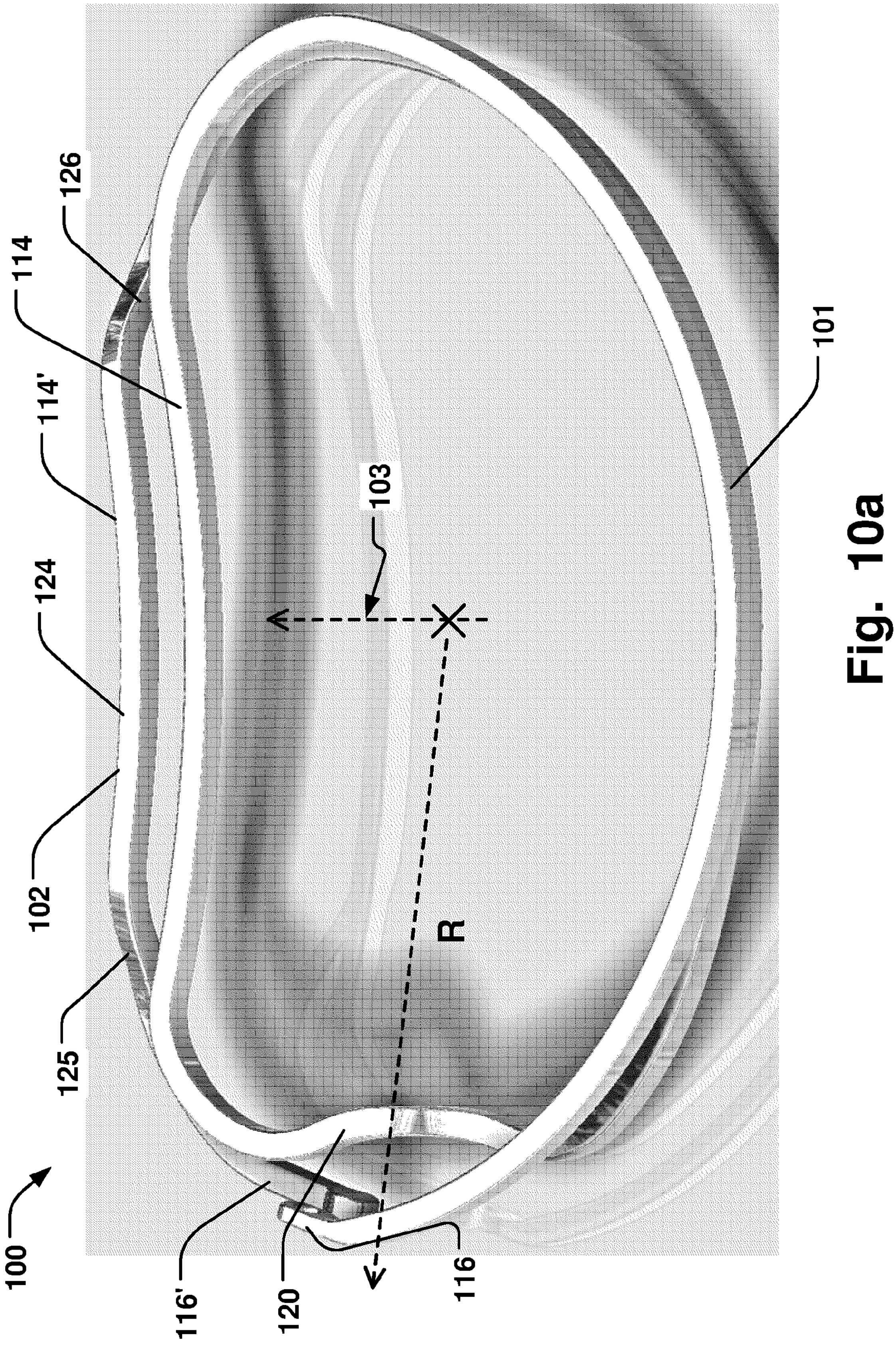
FIG. 10*a* is a schematic illustration of an annuloplasty device, in a perspective view, according to an example.
Figure 11:
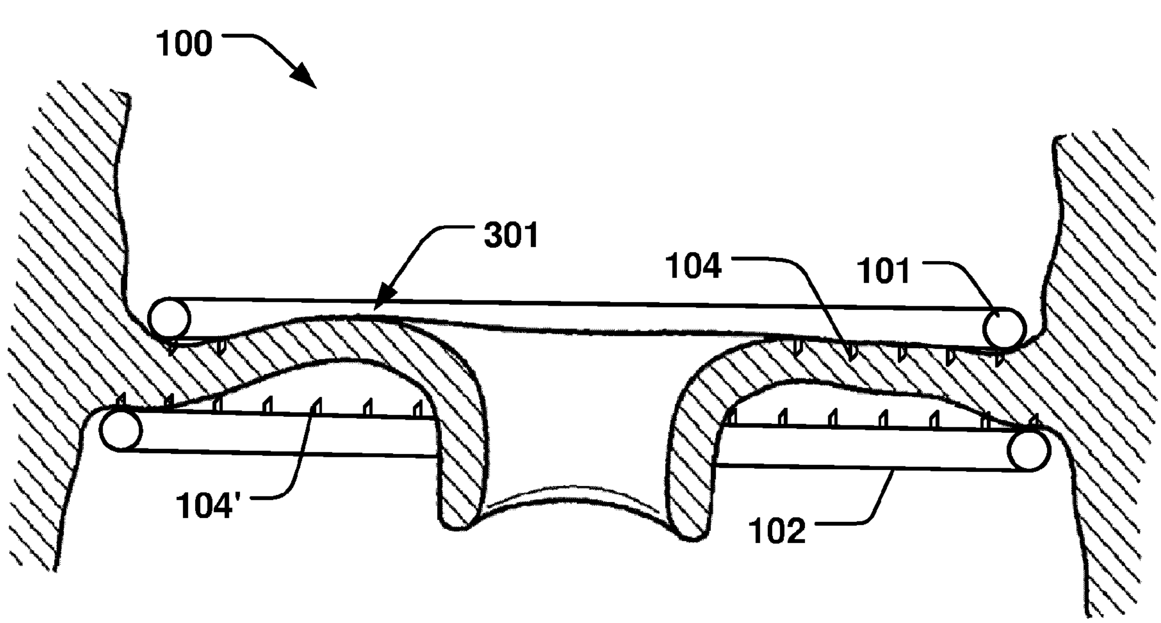
FIG. 11 is a schematic illustration of an annuloplasty device, in a side view, where the annuloplasty device is positioned above and below valve leaflets, according to an example of the disclosure.
Figure 12:
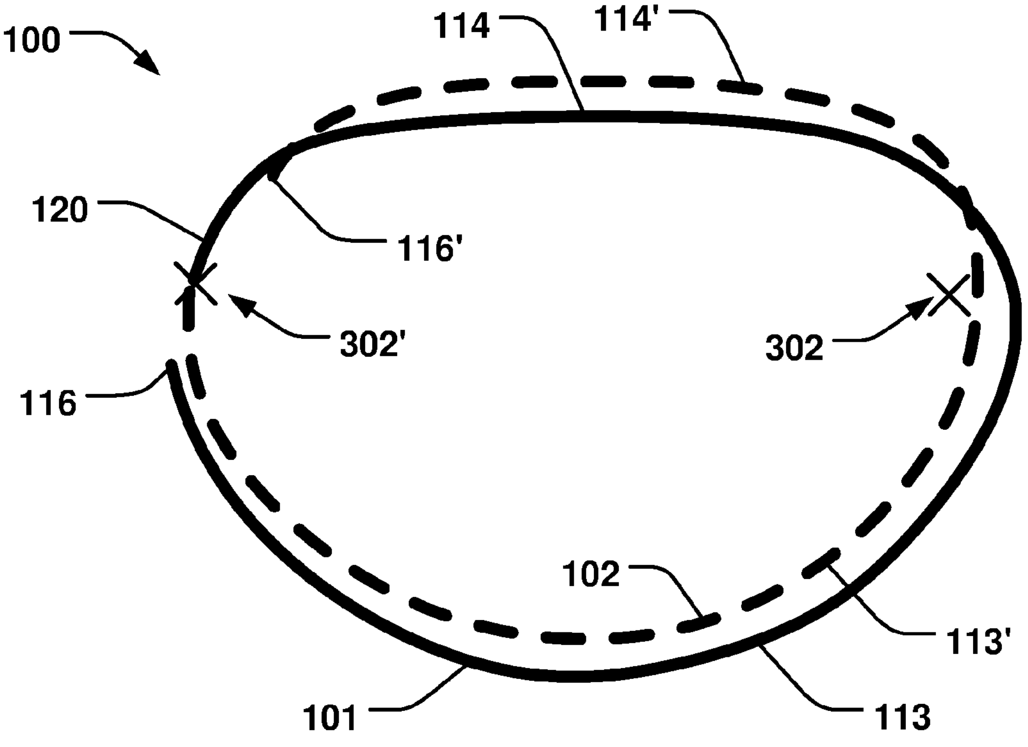
FIG. 12 is a schematic illustration of an annuloplasty device, in a top-down view, according to an example.

FIG. 1 schematically illustrates an example of an annuloplasty device 100 comprising a first support ring 101 and second support ring 102 which are adapted to be arranged as a coil, i.e. in a helix-shape, in a coiled configuration around a central axis 103, as illustrated in FIG. 1. The device 100 is arranged in the coiled configuration at least when in a relaxed state of the material from which the device 100 is formed, i.e. free from outside forces acting upon the device 100. The coil-shaped device 100 has two free ends 116, 116'. The first and second support rings 101, 102, and the respective free ends 116, 116', are configured to be arranged on opposite sides of native heart valve leaflets 301 of a heart valve, as illustrated in e.g. the side view of FIG. 11. As shown in FIG. 11, the first support ring 101 may be arranged on an atrial side of the heart valve, and the second support ring 102 may be arranged on a ventricular side (the second support ring 102 is also shown with dashed lines in the top-down view of FIG. 12, where the valve leaflets have been omitted). The second support ring 102 is illustrated with a dashed line and is in these examples arranged on the ventricular side of the heart valve, whereas the first support ring 101 is arranged on the atrial side of the heart valve (shown with solid line). The first support ring 101 may thus extend along the annulus of the heart valve on the atrial side. The transition point between the first and second rings 101, 102, is in the example of FIG. 12 at the commissure denoted 302'. FIGS. 1-8, 10, 11, show examples of an annuloplasty device 100 which may be arranged as illustrated in FIG. 12.

The first and second support rings 101, 102, are connected to form a coil- or helix shaped ring, as an integral continuous ring. The coil extends through the valve opening at a commissure 302', thereof, as schematically illustrated in FIG. 12. The first and second support rings 101, 102, may thus assume the coiled configuration also when in an implanted state. As explained further below, the device 100 may comprise a shape-memory material, so that the device 100 re-assumes the coiled configuration after having been delivered from a catheter (not shown) to the target site, after having been temporarily restrained in an elongated configuration of the catheter. The annuloplasty device 100, i.e. annuloplasty implant 100, may comprise a shape memory material, such as NiTiNol, or another suitable biocompatible alloy that can be heat-set in defined shapes, i.e. in a defined relaxed shape in absence of outside acting forces, as described further below, in a heat treatment procedure. The annuloplasty device 100 may pinch the tissue of the valve leaflets 301, between the first and second support rings 101, 102, i.e. with forces acting parallel with the central axis 103.

Figure 8:
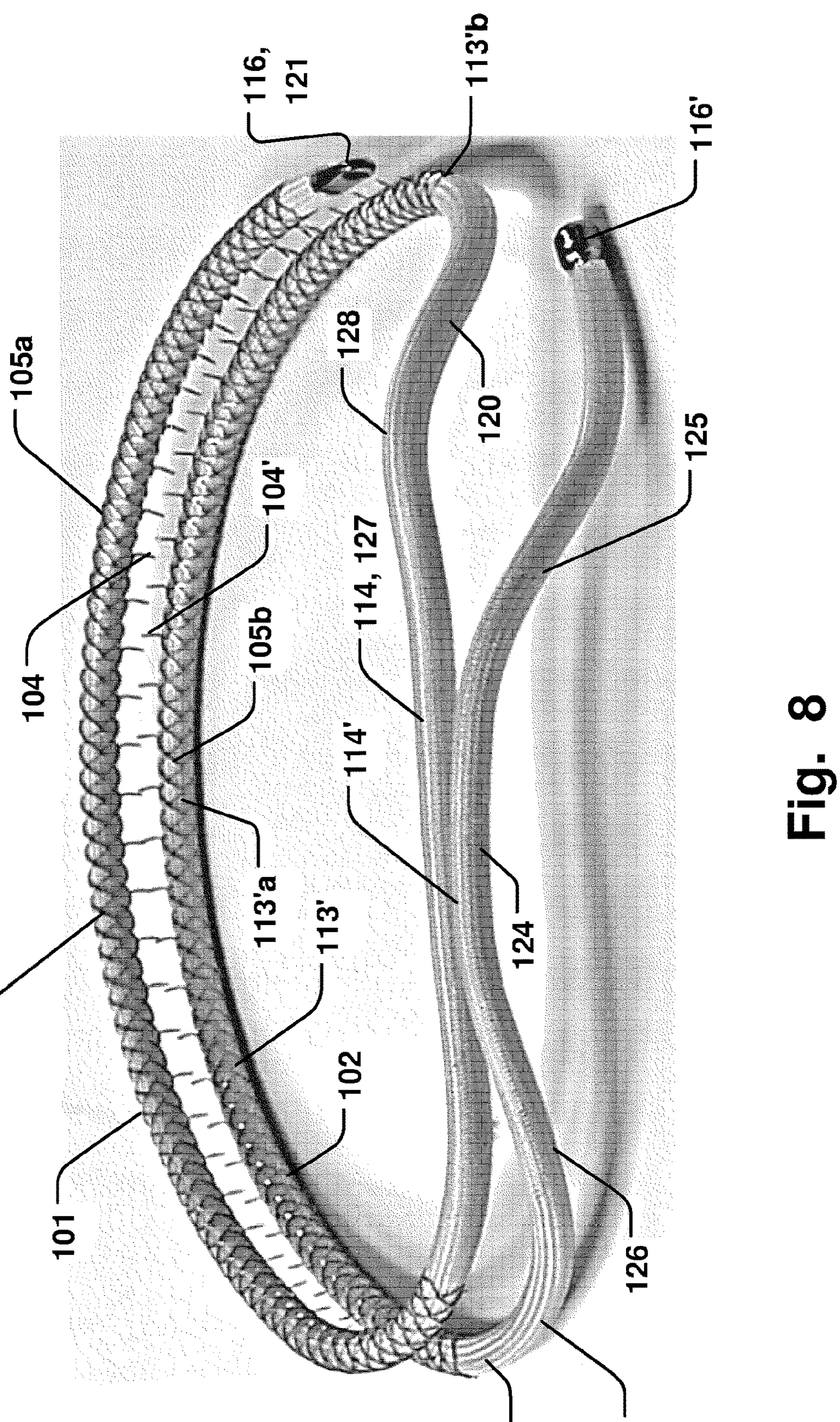
FIG. 8 is a schematic illustration of an annuloplasty device, in a perspective view, according to an example.

The annuloplasty device 100 may optionally comprise retention units 104, 104', as schematically illustrated in the perspective view of FIG. 8 and in the side view of FIG. 11. FIGS. 8 and 11 show examples where a plurality of retention units 104, 104', are arranged on the first and second support rings 101, 102. The device 100 may be in an elongated stretched configuration while being restrained in a catheter. However, as mentioned above, the device 100 assumes the coiled shape when released from the catheter, whereupon the retention units 104, 104', may engage the tissue on the atrial and ventricular sides of the heart valve, as exemplified in FIG. 11. The retention units 104, 104', are configured to engage the tissue of the valve and anchor the device 100 at the valve, and are described in more detail below.

The first support ring 101 transitions to the second support ring 102 over a transition section 120, as illustrated in e.g. FIGS. 1-4, 5*c*, 6-8, 10*a-b*. The transition section 120 is adapted to be arranged at a commissure 302, 302', of the heart valve leaflets, e.g. at a commissure 302' as illustrated in FIG. 12. The first and second support rings 101, 102, extend in respective first and second coil planes 101', 102', being essentially perpendicular to the central axis 103, as illustrated in e.g. FIG. 2*c*. The transition section 120 may bend at least partly along the central axis 103 so that the first coil plane 101' is separated a distance ($d_1$) from the second coil plane 102' along the central axis 103 (i.e. along a direction parallel to the central axis) at the transition section 120. Having such transition section 120 where the coil planes 101', 102', are locally displaced a distance ($d_1$), and at a position corresponding to the location of the commissure 302, 302', provides for improved accommodation of the first and second support rings 101, 102, to the anatomy at the opposite sides of the valve, in particular as the heart beats. Having a step-down in the coil planes 101', 102', or an "S-shape", or "Z-shape", of the support rings 101, 102, at the transition section 120 due to separation distance ($d_1$) provides for a better coaptation of the first and second support rings 101, 102, at the commissure 302, 302'. I.e. the risk of having the moving valve leaflets pulling on any of the support rings 101, 102, at the commissure 302, 302', is minimized because the first coil plane 101' of the first support ring 101 on the atrial side transitions to the second coil plane 102' of the second support ring 102 over a reduced distance at the transition section 120 due to the displacement ($d_1$) (i.e. corresponding to a local section 120 of increased pitch or rise of the coil formed by the adjacent support rings 101, 102). This means that the first and second support rings 101, 102, may conform better to the two opposite sides of the valve close to the commissure 302, 302'. The annuloplasty device 100 may thus be secured at the valve in a safer manner, while the risk of dislocations is minimized. The position of the transition section 120 may be varied depending on which commissure 302, 302', the first/second support rings 101, 102, extend through the valve leaflets. The transition section 120 may thus have an increased slope or pitch relative the central axis 103 compared to the remaining portions of the first and second support rings 101, 102.

Figures 2A, 2B:
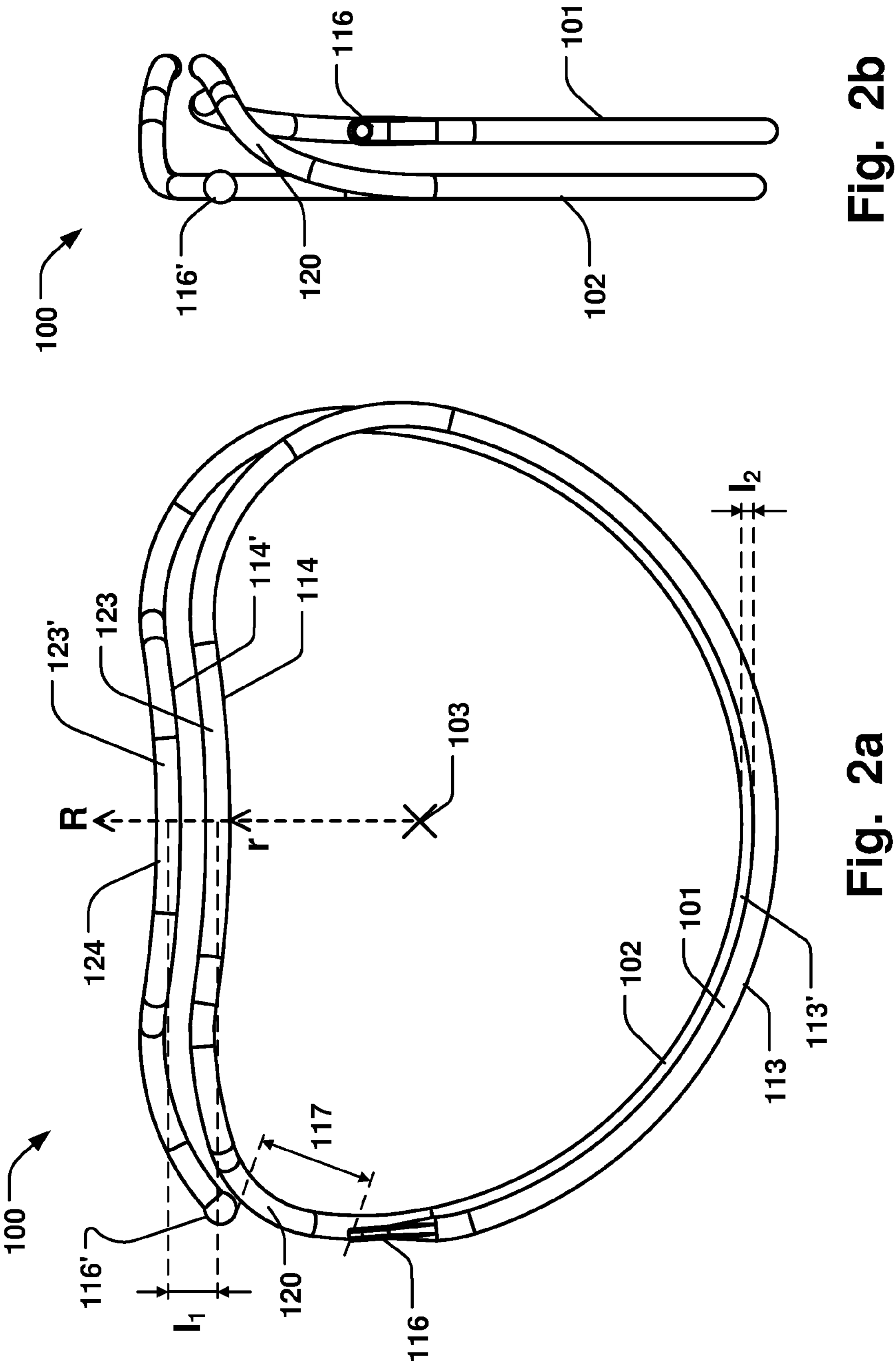
FIG. 2*a* is schematic illustration of the annuloplasty device in FIG. 1, in a top-down view, according to an example.
FIG. 2*b* is schematic illustration of the annuloplasty device in FIG. 2*a*, in a side view, according to an example.

The length of the transition section 120 may in one example correspond to approximately an off-set distance 117 between free ends 116, 116', as schematically illustrated in FIG. 2*a*. In one example the transition section 120 may be arranged after the first support ring 101 forms essentially one complete loop, as exemplified in FIGS. 1 and 2*a*.

The transition section 120 may bend at least partly along a radial direction (R), where the radial direction (R) is perpendicular to the central axis 103, so that the transition section 120 is concave towards the radial direction (R). FIG. 10*a* illustrates an example of such concave bend, or "C-curve", of the transition section 120 towards the radial direction (R). This may provide for further improving the coaptation of the first and second support rings 101, 102, to the valve anatomy close to the commissure 302, 302'. The risk of having a disadvantageous force transfer or friction between the moving valve leaflets and any of the support rings 101, 102, at the commissure 302, 302', can be minimized. The first and second support rings 101, 102, may extend along the annulus as far as possible while extending through the commissure 302, 302', with minimized impact on the valve motion, as the concave bend of the transition section 120 allows for adapting to anatomies where the commissure 302, 302', is located closer to the central axis 103 than the annulus. The annuloplasty device 100 may thus be secured at the valve in a further improved manner, while the risk of dislocations in the long term is minimized.

The first support ring 101 may comprise a first posterior bow 113 and a first anterior portion 114. The second support ring 102 may comprise a second posterior bow 113' and a second anterior portion 114'. The first and second posterior bows 113, 113', may be adapted to conform to a posterior aspect of the heart valve, i.e. along the posterior leaflet, having a bow-shaped extension. The first and second anterior portions 114, 114', may each have a straighter extension or at least an extension which is less bent than the bow-shaped posterior sides 113, 113'. This is exemplified in e.g.

FIGS. 1, 2*a*, 8. The first and second anterior portions 114, 114', may thus be adapted to conform to an anterior aspect of the heart valve, i.e. along an anterior leaflet.

Figure 5A:
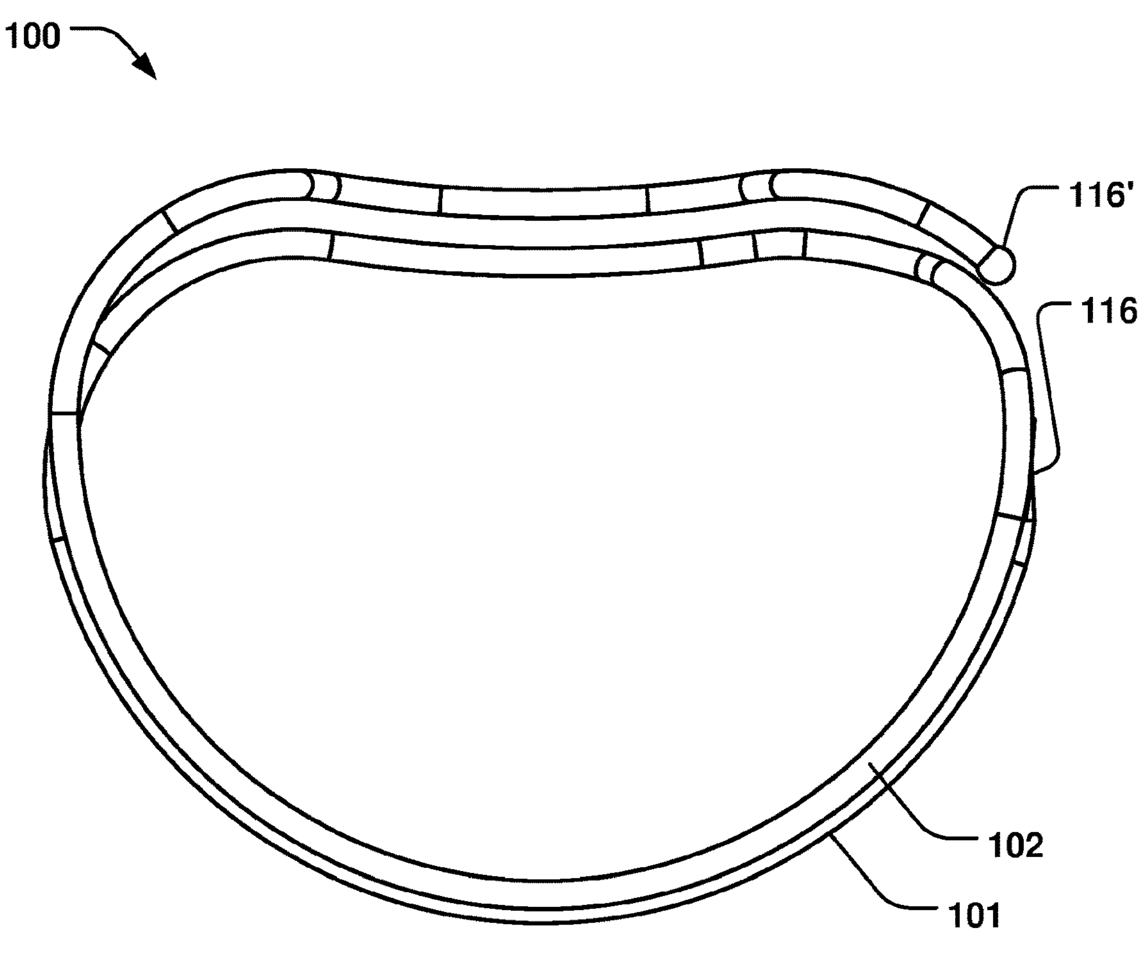
FIG. 5*a* is a schematic illustration of the annuloplasty device in FIG. 3, in a top-down view, according to an example.
Figure 5B:
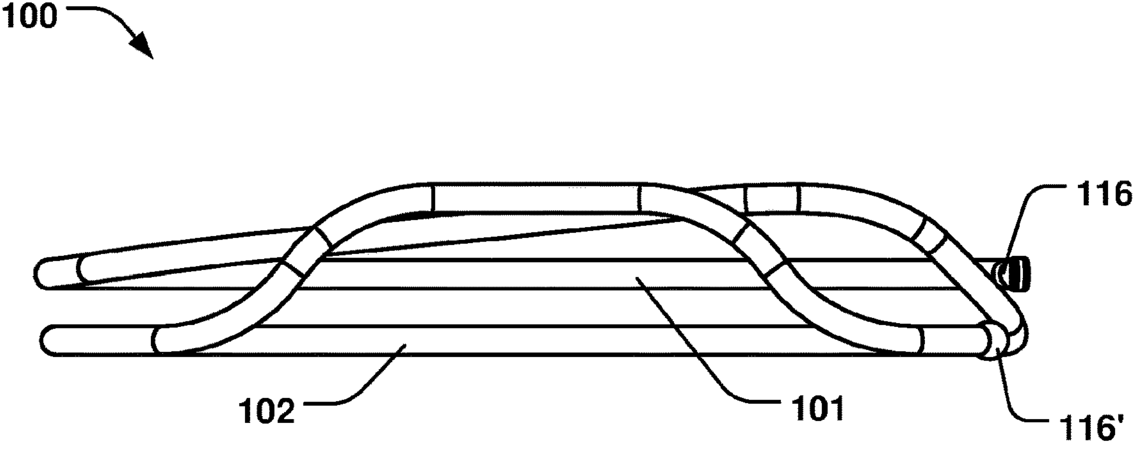
FIG. 5*b* is schematic illustration of the annuloplasty device in FIG. 5*a*, in a side view, according to an example.
Figure 5C:
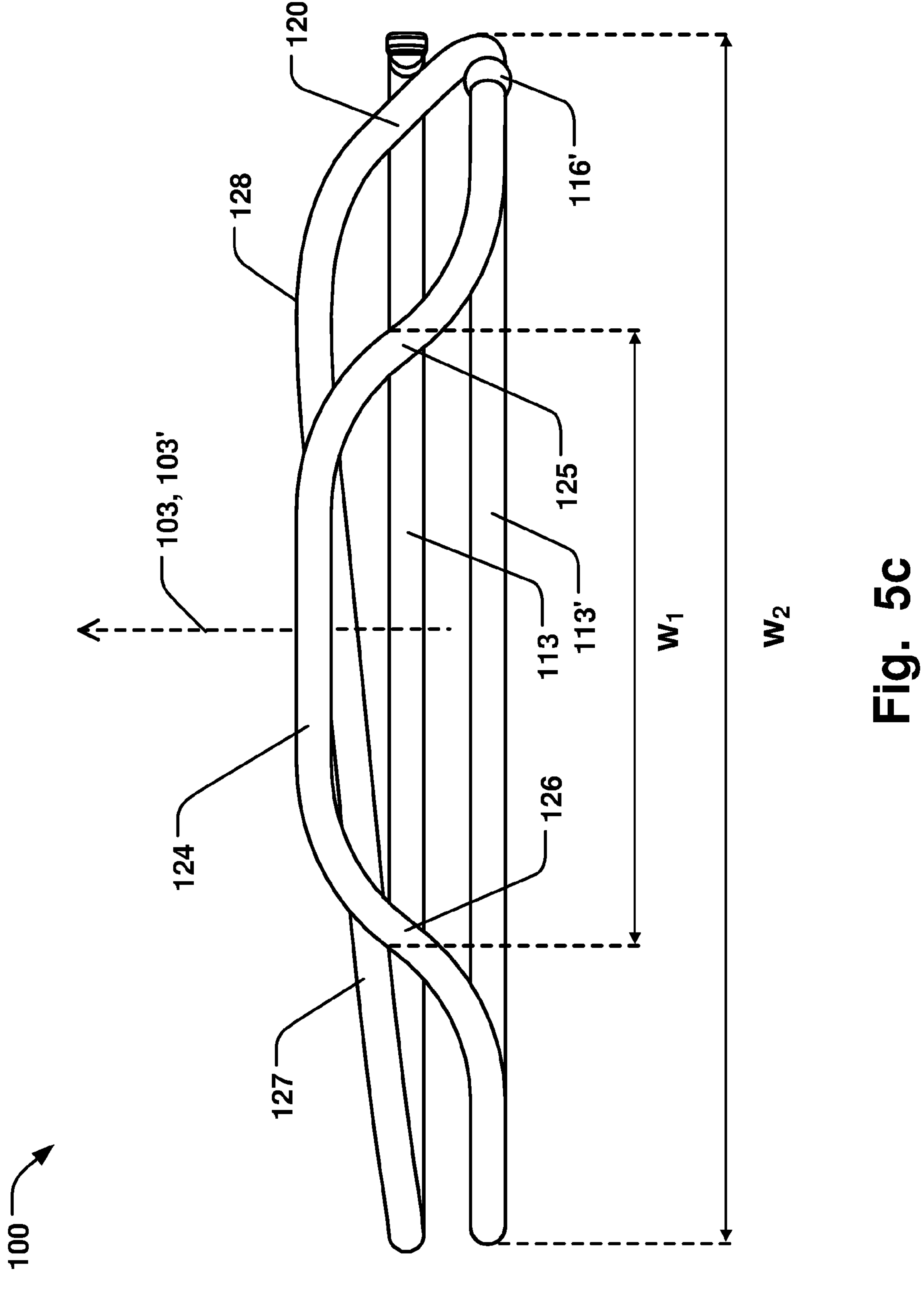
FIG. 5*c* is an enlarged view of FIG. 5*b;*
Figure 5D:
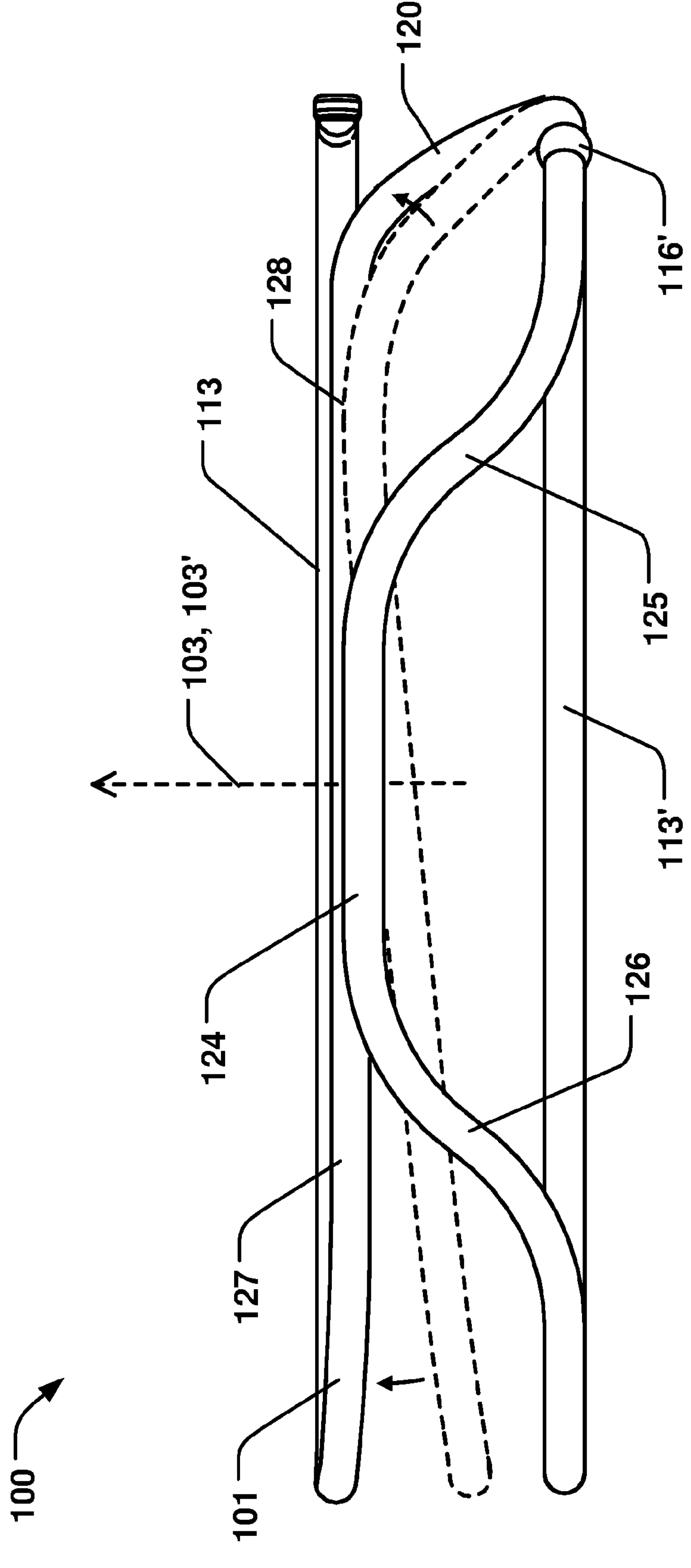
FIG. 5*d* is a schematic illustration of the annuloplasty device in FIG. 5*c* in a loaded state where first and second support rings thereof are pushed apart, according to one example.

The first anterior portion 114 of the first support ring 101 may comprise a tilted section 127, which is angled in the axial direction 103'. The axial direction 103' is orthogonal to the first and second coil planes 101', 102', an is directed from the second support ring 102 to the first support ring 101. The tilted section 127 is angled such that it raises above the first posterior bow 113 in the axial direction 103', as schematically illustrated in FIG. 5*c*. A perspective view of the tilted section 127 is further schematically illustrated in FIG. 1. Having a tilted section 127 of the first anterior portion 114 provides for an improved coaptation of the annuloplasty device 100 to the anterior portion of the heart valve on the atrial side with reduced risk of interference with the anterior leaflet of the mitral valve. As the first and second support rings 101, 102, are positioned on opposite sides of the valve leaflets, as schematically indicated in FIG. 11, the valve tissue push the first and second support rings 101, 102, apart. The tilted section 127 may be movable about the transition section 120, in the axial direction 103', so that the tilted section 127 is movable to extend essentially in parallel with the first and/or second coil planes 101', 101', of the first and second posterior bows 113, 113'. FIG. 5*d* is a schematic illustration of such movement, where the first and second support rings 101, 102, are pushed apart, causing the tilted section 127 to assume a position where it is essentially in parallel with the first and second posterior bows 113, 113'. The dashed lines in FIG. 5*d* correspond to the relaxed position of the annuloplasty device 100 shown in FIG. 5*c*, where no external forces act upon the annuloplasty device 100. The indicated arrows show the movement of the first support ring 101 and the tilted section 127 thereof about the transition section 120. Having a tilted section 127 as described provides for accommodating the tissue between the first and second support rings 101, 102, with reduced interference with the anterior valve leaflet. As the annuloplasty device 100 is inserted into the implanted position the transition section 120 is inserted into place through the commissure 302' (FIG. 12). The first anterior portion 114 in the atrium will transition to the second posterior bow 113' in the ventricle over the transition section 120 (see further perspective view of FIG. 1). Having a first anterior portion 114 raising above the first coil plane 101' of the first posterior bow 113, by having a tilted section 127 as described above, allows for the second support ring 102 and the second posterior bow 113' to move downwards, i.e. opposite the axial direction 103', to accommodate leaflet tissue upon said insertion and pull the tilted section 127 to a position in parallel with the first and/or second coil plane 101, 102', as illustrated in FIG. 5*d*. The risk of having the first anterior portion 114 applying too high pressure onto the valve tissue on the atrial side, in particular close to the commissure 302', can thereby be reduced. The first anterior portion 114 may instead be arranged in a parallel position when implanted so that an even pressure is applied to the tissue along the length of the first anterior portion 114. The risk of damage to the leaflet tissue is thus reduced.

The tilted section 127 may further assume a position essentially in parallel with an inverted section 124 of the second anterior portion 114' when the first and second support rings 101, 102, are separated to accommodate tissue, as further illustrated in FIG. 5*d*. An even and effective retention force to the valve tissue may thus be provided between section 127 of the first anterior portion 114 and the inverted section 124. A more secure and reliable implantation is thus provided. The inverted section 124 is described in more detail below.

Figure 7:
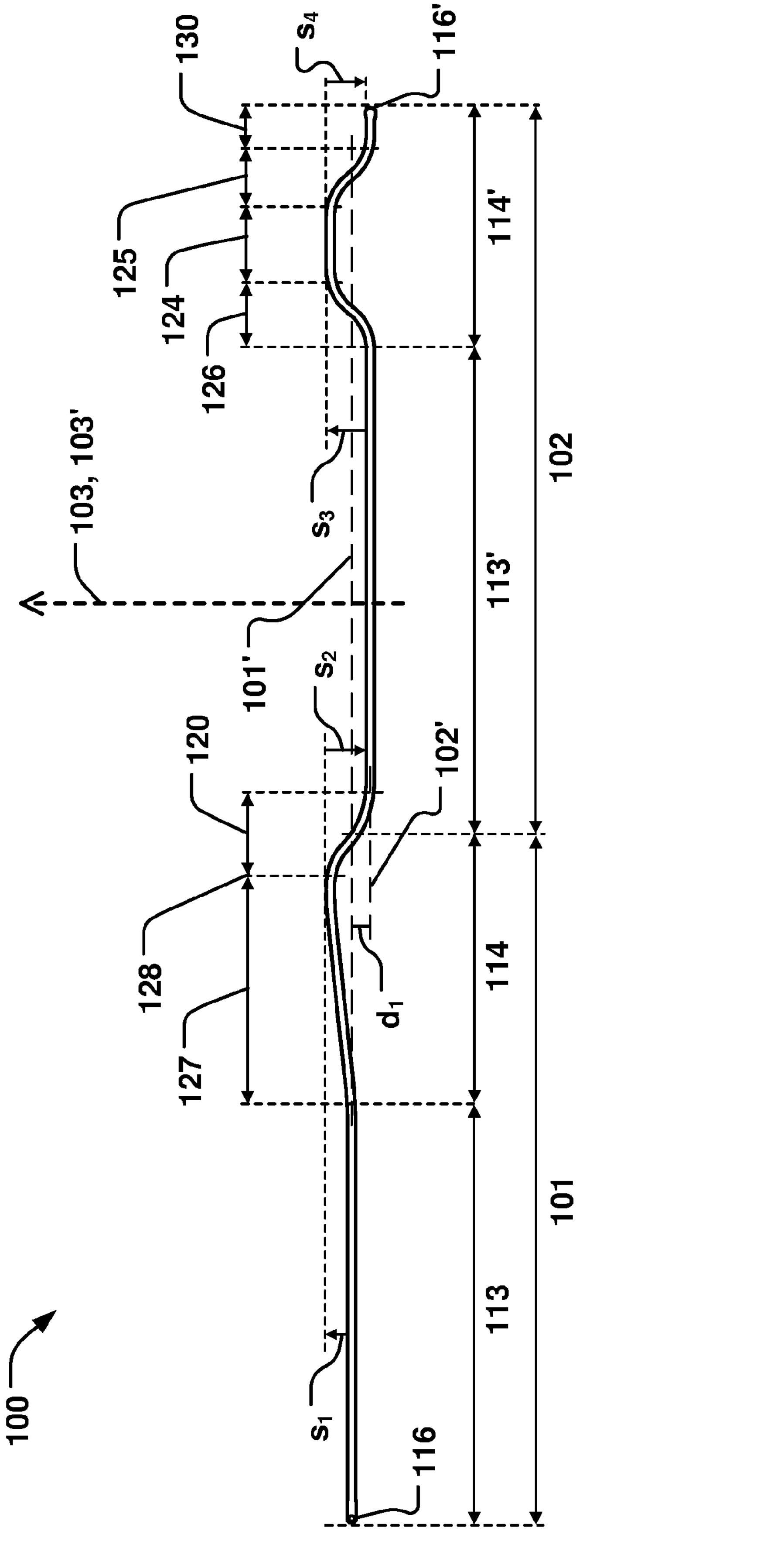
FIG. 7 is a schematic illustration of an annuloplasty device, in a side view, where the first and second support rings of the annuloplasty device have been arranged to extend in a stretched-out configuration, according to an example.

FIG. 7 is a view of the annuloplasty device 100 according to an example where the first and second support rings 101, 102, have been unfolded or un-coiled to assume a stretched-out elongated configuration. The curvatures and relative positions of the first and second anterior portions 114, 114', are illustrated in relation to the first and second posterior bows 113, 113'. The relative positions are shown in the axial direction 103' of the central axis 103 as well as in a direction perpendicular to the axial direction 103', i.e. horizontally in FIG. 7. The extension of the first and second coil planes 101', 102', relative the axial direction 103', are also indicated for reference. As shown in the example of FIG. 7, the tilted section 127 is angled from the first posterior bow 113, i.e. from the first coil plane 101', towards the axial direction 103'. Moving from the left to the right in FIG. 7, the tilted section 127 joins to the transition section 120 which curves in a direction against the axial direction 103' towards to the position of the second posterior bow 113'. The second posterior bow 113' (or the second coil plane 102' thereof) and the tilted section 127 are thus arranged on opposite sides of the first posterior bow 113 (or the first coil plane 101' thereof). This further provides for the indicated separation distance $d_1$ between the first and second coil planes 101', 102'.

Figures 4A, 4B:
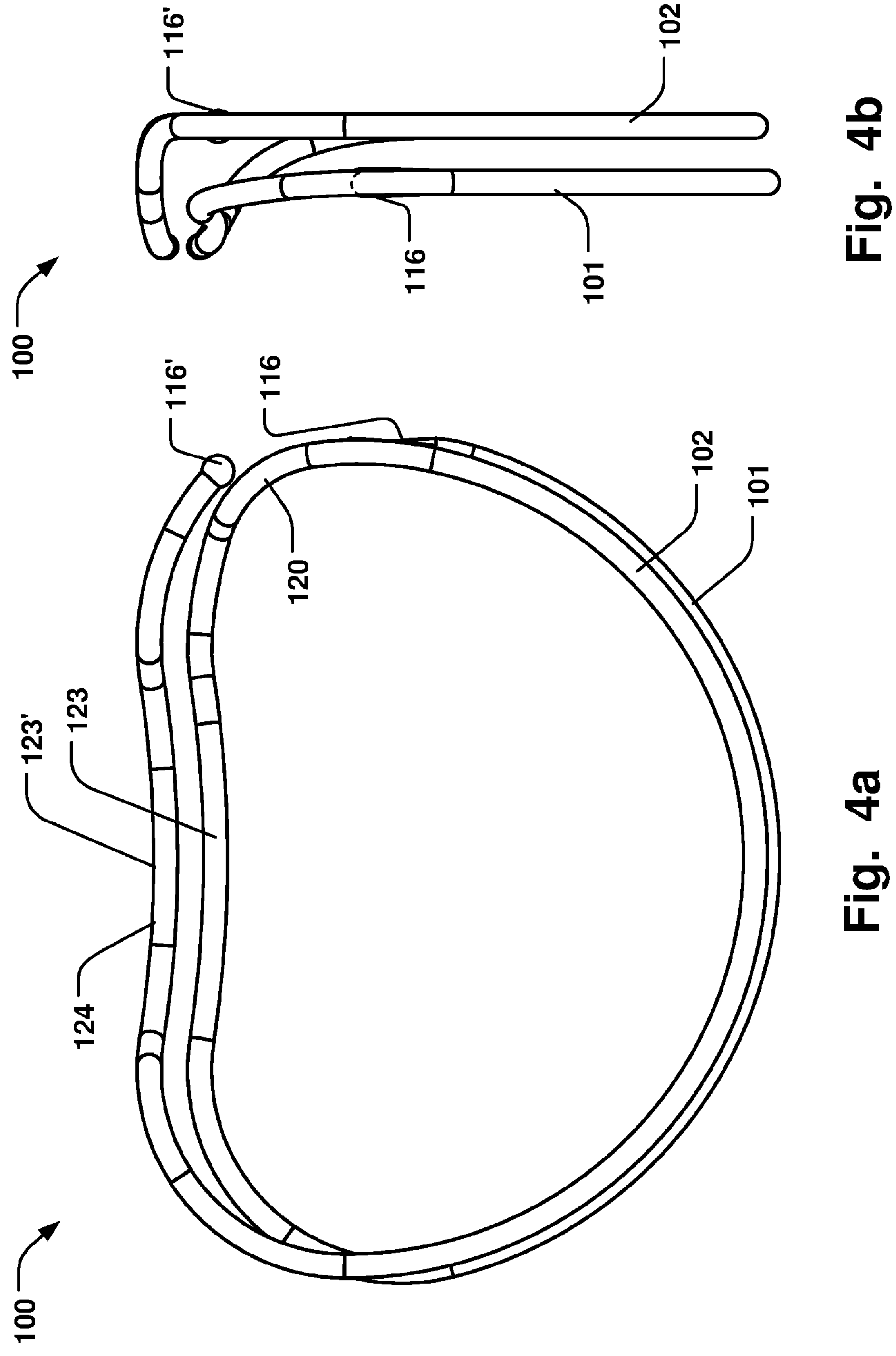
FIG. 4*a* is schematic illustration of the annuloplasty device in FIG. 3, in a top-down view, according to an example.
FIG. 4*b* is schematic illustration of the annuloplasty device in FIG. 4*a*, in a side view, according to an example.
Figure 4C:
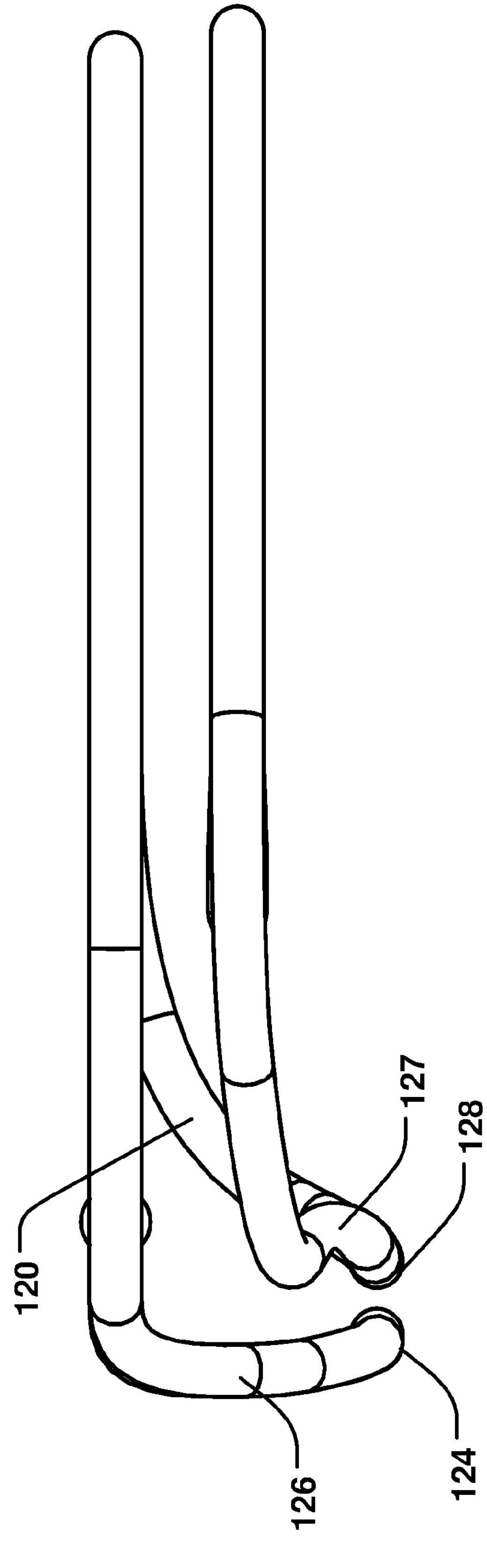
FIG. 4*c* is an enlarged view of FIG. 4*b;*

The tilted section may raise to an apex 128 of maximum separation from the first posterior bow 113 along the axial direction 103', as schematically indicated in e.g. the side views of FIGS. 4*c*, 5*c*, and 7. The first anterior portion 114 transitions gradually with a smooth curved shape from the apex 128 to the transition section 120. The tilted section 127 may extend in an essentially linear shape from the first posterior bow 113 to the apex 128, as schematically illustrated in the examples of FIGS. 5*c* and 7. The first anterior portion 114 may thus provide an incremental and linear increase in the separation from the first coil plane 101', towards the apex 128. As the second support ring 102 is inserted into the ventricular side it pulls the tilted section 127 down towards the valve tissue via the transition section 120, so that the tilted section 127 assumes a position essentially in parallel with the first and second posterior bows 113, 113' (FIG. 5*d*). Having a linear shape of the tilted section 127 allows for the first anterior portion 114 to apply an even retention force to the tissue along its length as the tilted section 127 assumes the essentially parallel position discussed in relation to FIG. 5*d* above. Thus, an improved and more secure fit to the surrounding anatomy is provided when the first anterior portion 114 is positioned at the anterior side of the valve in the atrium.

The advantageous features of the tilted section 127 as described above provides for an improved annuloplasty device 100 with a stronger retention into the tissue, also in absence of the aforementioned transition section 120. The tilted section 127 thus also provides for a separate aspect of the invention.

Figure 2C:
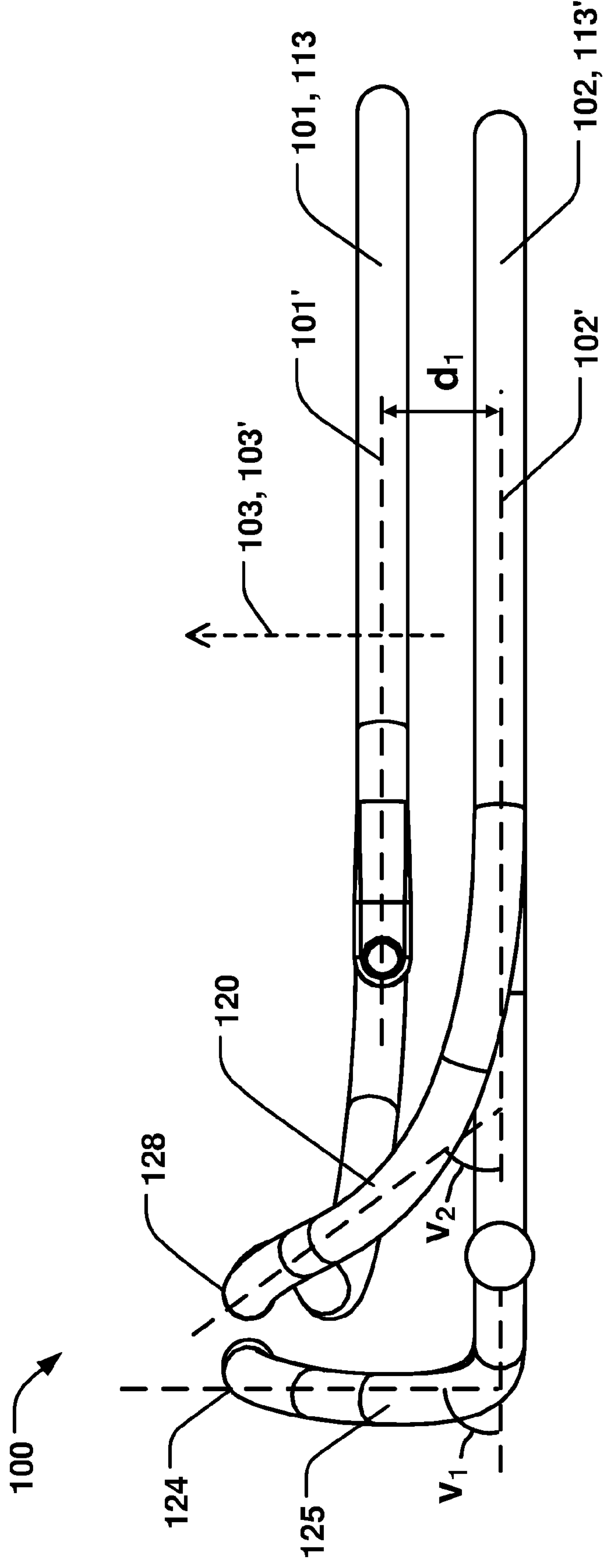
FIG. 2*c* is an enlarged view of FIG. 2*b;*

In the examples illustrated in e.g. FIGS. 1, 2*c* and 5*c*. The transition section 120 connects the apex 128 and the second support ring 102. As illustrated, the transition section 120 may form a smooth curve from the apex 128 towards the second posterior bow 113' and the associated second coil plane 102'. This provides for a reliable and non-traumatic coaptation to the anatomy at the commissure 302', through which the transitions section 120 is arranged.

As elucidated above, a separation ($s_1$) between the apex 128 and the first posterior bow 113 in the axial direction 103' may be less than a separation ($s_2$) between the apex 128 and the second posterior bow 113' in the axial direction 103'. A tilted section 127 as described above may thus be provided while maintaining a separation distance $d_1$ between the first and second coil planes 101', 102'.

The second anterior portion 114' may comprise an inverted section 124 extending in parallel with the first and second coil planes 101', 102'. The inverted section 124 and the second posterior bow 113' extend on opposite sides of the first posterior bow 113, of the first support ring 101, with respect to the direction of the central axis 103, as schematically illustrated in e.g. the side views of FIG. 20, 5*c* and the perspective view of FIG. 1. The inverted section 124 is further illustrated in the view of FIG. 7, showing the first and second support rings 101, 102, in an un-coiled elongated configuration. Having a section of the second anterior portion 114' raised above the first support ring 101, i.e. above the first posterior bow 113, as illustrated in FIG. 5*c*, provides for increasing the compression force along the first and second anterior portions 114, 114', when the first and second support rings 101, 102, are arranged on opposite sides of the heart valve. When the annuloplasty device 100 is positioned at the heart valve, with the second support ring 102 arranged on the ventricular side, the inverted section 124 will be pushed down, i.e. against the axial direction 103' in FIG. 5*c*, when forced into place at the heart valve. The second anterior portion 114' will thus be placed on the ventricular side of the heart valve. Having an inverted section 124 in the relaxed state of the annuloplasty device 100 means that the second anterior portion 114' will strive towards the relaxed shape, free from outside forces, as illustrated in e.g. FIG. 5*c*. The inverted section 124 of the second anterior portion 114' will thus strive to a position above the first posterior bow 113 (as shown in FIG. 5*c*), with respect to the central axis 103. This will cause an increased pressure on the valve tissue along the inverted section 124, and between the first and second anterior portions 114, 114', when the annuloplasty device 100 is implanted. This provides for a more secure fixation of the annuloplasty device 100 at the heart valve. Having an inverted section 124 as described above provides for an effective anchoring of the second anterior portion 114' along the aorto-mitral curtain which is the junction between the base of anterior mitral leaflet and aortic root. The inverted section 124 may be effectively anchored behind the aorto-mitral curtain. The inverted section 124 provides for creating a retention force to the tissue which prevents rotation or slipping of the annuloplasty device 100 around central axis 103, since the inverted section 124 forms an angle ($v_1$) with the coil planes 101', 102' (see FIG. 2*c*). The inverted section 124 may thus exert a force onto the tissue which has a force vector component extending in parallel with the coil planes 101', 102'. The aforementioned force may be applied along the extension of the inverted section 124 and/or any of the curved transition sections 125, 126 thereof. This provides for a more secure, robust, and reliable anchoring of the annuloplasty device at the heart valve. This provides for an improved function and safety for the patient, both short term and long term. The implantation procedure may thus be accomplished in less time and with improved control. A secure positioning of the first and second support rings 101, 102, at the opposite sides of the heart valve is facilitated.

Turning again to FIG. 5*c*, the inverted section 124 may raise above the first posterior bow 113 in the axial direction 103' along a width ($w_1$) of the invented section 124. The aforementioned width ($w_1$) may be a fraction of a width ($w_2$) of the first or second support rings 101, 102, in a direction essentially in parallel with the first or second anterior portions 114, 114', as schematically illustrated in the example of FIG. 5*c*. The fraction may be in the range 30-80%. I.e. width $w_1$ may be 30-80% of width $w_2$. This may provide for an advantageous compression of the tissue between the first and second anterior portions 114, 114'. The width $w_1$ may in some examples be in the range 50-60% of width $w_2$, for a particularly advantageous and reliable positioning of the first and second anterior portions 114, 114', on the opposite sides of the valve leaflets.

In one example the inverted section 124 may be arranged symmetrically with respect to the central axis 103, e.g. essentially centrally with respect to the width $w_2$ of the support rings 101, 102, as exemplified in FIG. 5*c*. The transition sections 125, 126, forming the curvature of the inverted section 124 along the axial direction 103' may also be essentially symmetrically shaped relative the central axis 103, with respect to the respective degree of inclination and declination from the second coil plane 102', as illustrated in the example of FIG. 5*c*. This provides for an advantageous compression of the tissue between the first and second anterior portions 114, 114'. Turning to the top-down view of FIG. 2*a*, the curvature of the second anterior portion 114' in the coil planes 101, 102', i.e. orthogonal to central axis 103, may be essentially symmetrical with respect to a radial direction (R) extending vertically from the center axis 103 in FIG. 2*a*. The free end 116' may be arranged radially outside the first anterior portion 114. This provides for improved accommodation of the free end 116' into the subannular groove. The curvature of the first anterior portion 114 in the coil planes 101, 102', may also be essentially symmetrical with respect to a radial direction (R) extending vertically from the center axis 103 in FIG. 2*a*.

Turning again to the example of FIG. 7, a separation ($s_2$) between the apex 128 and the second posterior bow 113' in the axial direction 103' may correspond essentially to a separation ($s_3$) between the inverted section 124 and the second posterior bow 113' in the axial direction 103'. Further, it is illustrated in the example side view of FIG. 2*c* that the apex 128 and the inverted section 124 may be arranged at a similar height with respect to the second coil plane 102' and the axial direction 103'. Such height of the apex 128 allows for advantageously accommodating the movement between the first and second support rings 101, 102, as tissue is pinched therebetween, while attaining an even distribution of the compression force between and along the first and second anterior portions 114, 114', as described above in relation to FIG. 5*d*.

The first and second support rings 101, 102, have respective first and second free ends 116, 116', configured to be arranged on opposite sides of the native heart valve leaflets, as described above. In one example, the inverted section 124 transitions to the free end 116' of the second support ring 102 over an anterior transition section 125, as schematically illustrated in the side view of FIG. 5*c* and the perspective view of FIG. 3. The anterior transition section 125 bends at least partly along the central axis 103 so that the free end 116' of the second support ring 102 is arranged on the same side of the first posterior bow 113, of the first support ring 101, as the second posterior bow 113', with respect to the direction of the central axis 103. Having the free end 116' recessed from the inverted section 124, against the axial direction 103', provides for a further improved accommodation to the anatomy of the heart valve. For example, the free end 116' may be positioned to sit in the subannular groove by having such anterior transition section 125. The anterior transition section 125 may be arranged at the end of the first and second anterior portions 114, 114', in a direction towards the free end 116', as further exemplified in FIGS. 1 and 3. The second support ring 102 may comprise a free end 116' which is curved towards the free end 116 of the first support ring 101, in the plane of the coil planes 101', 102', as further exemplified in FIG. 2*a*. The second support ring 102 may thus be bent after the second anterior portion 114', i.e. adjacent the position of the commissure. In one example, the anterior transition section 125 is arranged towards the end of the second anterior portion 114', in a direction towards the free end 116', so that essentially the entire curved part of the second support ring 102, after the second anterior portion 114', is arranged at the same side of the first support ring 101 as the second posterior bow 113' with respect to the direction of the central axis 103 (FIG. 5*c*). This provides in some examples for an improved fit to the surrounding anatomy of the annuloplasty device 100.

In one example the anterior transition section 125 may be curved such that the free end 116' is positioned with the same separation ($d_1$) from first coil plane 101' as the second posterior bow 113'. I.e. the free end 116' is arranged at the same position as the second posterior bow 113' with respect to the axial direction 103' (FIG. 5*c* and FIG. 7). The anterior transition section 125 may comprise a smooth curvature forming a smooth transition from the inverted section 124 to an end section 130 of the second support ring 102, as exemplified in e.g. FIG. 7. The end section 130 may be aligned to extend in the second coil plane 102', and terminating with the free end 116'.

Figure 3:
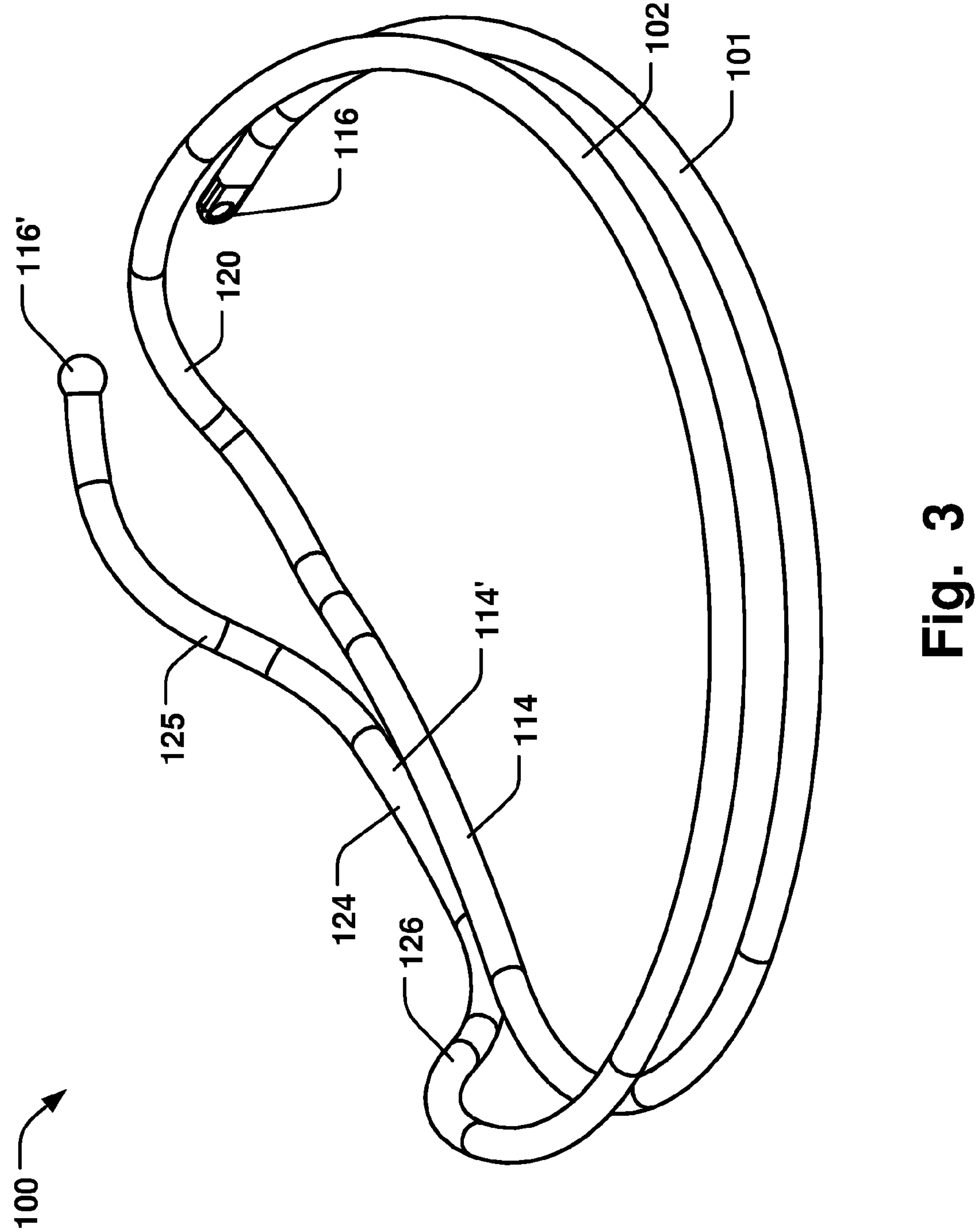
FIG. 3 is a schematic illustration of an annuloplasty device, in a perspective view, according to an example.

The second anterior portion 114' may comprise a second anterior transition section 126, where the second support ring 102 is bent in a direction along the central axis 103 to form the step-up curve of the inverted section 124, as exemplified in FIGS. 5*c* and 7. The step-down curve of the inverted section 124, towards the free end 116', may consequently be formed by the anterior transition section 125 described above. The advantageous features of the inverted section 124, and anterior transition sections 125, 126, described in relation to FIGS. 1, 3, 5*c*, provides for an improved annuloplasty device 100 with a stronger retention into the tissue, also in absence of the aforementioned transition section 120 and/or tilted section 127. The inverted section 124 thus also provides for a separate aspect of the invention.

Turning to FIG. 2*c*, the inverted section 124 may be angled from the second coil plane 102' towards the axial direction 103' with a first angle ($v_1$). The transition section 120 may be angled from the second coil plane 102' towards the axial direction 103' with a second angle ($v_2$). The second angle ($v_2$) may be an acute angle, as schematically illustrated in FIG. 2*c*. The second angle ($v_2$) may be less than the first angle ($v_1$), as further illustrated in FIG. 2*c*. This provides for an advantageous coaptation of the annuloplasty device 100 to the anatomy around the commissure 302' as well as a reliable compression of the tissue between the first and second anterior portions 114, 114'. In one example, the inverted section 124 may extend in a direction essentially perpendicular to the second coil plane 102'. I.e. the first angle $v_1$ may be an essentially right angle to the second coil plane 102'. This provides for an effective anchoring of the annuloplasty device 100 along the anterior side of the valve.

At least part of the first anterior portion 114 and/or the second anterior portion 114' may be curved to form a respective concave section 123, 123', being concave towards a radial direction (R), where the radial direction (R) is perpendicular to the central axis 103, as schematically illustrated in FIG. 10*a*. This provides for further improving the accommodation of the first and second support rings 101, 102, to the anatomy of the valve and its annulus. E.g. the concave sections 123, 123', may provide for a better accommodation to the anatomy around the rounded aortic valve. A more secure attachment of the annuloplasty device 100 is achieved, and long-term reliability of the implantation.

The first anterior portion 114 may be displaced a distance ($I_1$) from the second anterior portion 114' along a radial direction (R) so that at least part of the second anterior portion 114' extends with a greater radius (r) from the central axis 103 than the first anterior portion 114, as schematically illustrated in FIG. 2*a*. Thus, when the first support ring 101 is arranged on the atrial side and the second support ring 102 is arranged on the ventricular side, the second anterior portion 114' of the second support ring 102 will extend with a greater radius from the central axis 103 than the first anterior portion 114 of the first support ring 101. Having a greater radius of the second support ring 102 on the ventricular side provides for an effective pinching of the valve tissue at the aorto-septal wall, and thus a more secure anchoring of the annuloplasty device 100.

As schematically illustrated in FIG. 2*a*, the first posterior bow 113 may be displaced a distance ($I_2$) from the second posterior bow 113' along a radial direction (R). The radial direction (R) is perpendicular to the central axis 103. The off-set between the first and second posterior bows 113, 113', provides for an improved fixation of the annuloplasty device 100 on a downsized posterior annulus and thus a more effective anchoring of the annuloplasty device 100. At least part of the first posterior bow 113 may thus extend with a greater radius (r) from the central axis 103 than the second posterior bow 113'. Having the first support ring 101 extending with a greater radius in the radial direction along the posterior bow 113 on the atrial side compared to the posterior bow 113' of the second support ring 102 on the ventricular side provides for an improved coaptation to the anatomy around the valve on the ventricular side, and thus a more secure anchoring of the annuloplasty device 100. Less interference with the native leaflets and chordae may be provided. Circumflexing of the chordae may also be facilitated. In one example the first posterior bow 113 may be displaced from the second posterior bow 113' with a distance ($I_2$) being less than the thickness, i.e. diameter of the cross-section, of the first and/or second posterior bow 113, 113', in the direction of the coil planes 101', 102'. This provides for avoiding having a "scissor"-effect on the tissue pinched between the first and second posterior bows 113, 113'. The risk of tissue abrasion or cutting may thus be reduced. The distance 12 may in one example correspond to half the diameter of the first and/or second posterior bow 113, 113'.

In another example however it should be understood that at least part of the second posterior bow 113' may extend with a greater radius (r) from the central axis 103 than the first posterior bow 113.

The advantageous features of having displacement distances ($I_1$, $I_2$), as described in relation to FIG. 2*a* provides for an improved annuloplasty device 100 with an improved anchoring into the tissue. The displacement distances ($I_1$, $I_2$) thus also provide for a separate aspect of the invention.

In one example, the first and second support rings 101, 102, comprises a resilient shape-memory material and may be movable along the central axis 103 to pinch the valve leaflets from opposite sides.

In the examples of FIGS. 1-6, 8, 10-12, the length of the first and second support rings 101, 102, form essentially two complete loops. This provides in some examples for an improved anchoring of the annuloplasty device 100 to the heart valve. In some situations, an off-set distance 117 between free ends 116, 116', as schematically illustrated in FIG. 2*a* may be advantageous.

Figure 6:
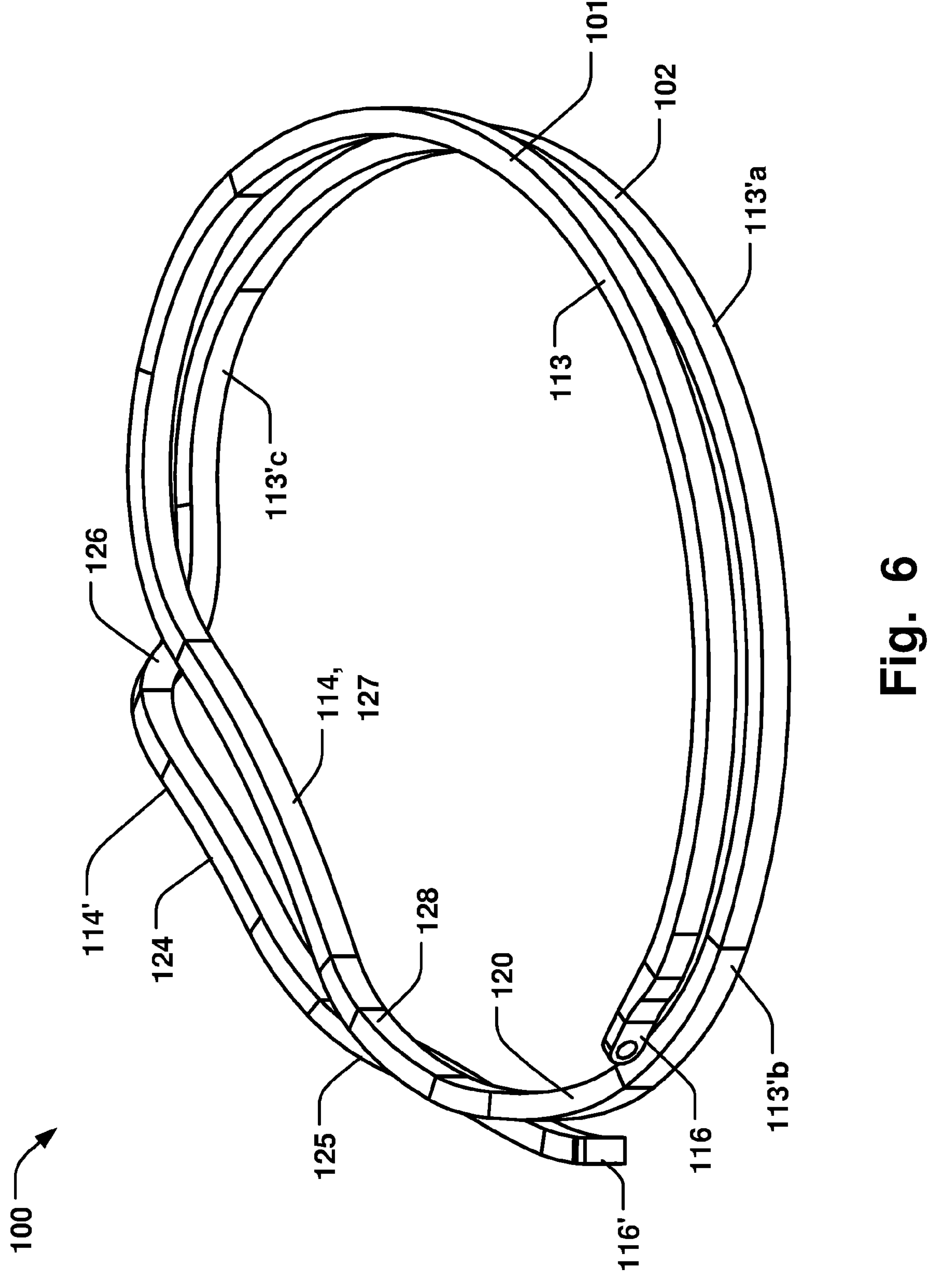
FIG. 6 is a schematic illustration of an annuloplasty device, in a perspective view, according to an example.

The second posterior bow 113' may comprise a central posterior arch 113'*a*, and further a first commissure section 113'*b* and a second commissure section 113'*c* on either side of the central posterior arch 113'*a*, as schematically illustrated in FIG. 6. The first support ring 101 transitions to the first commissure section 113'*b* over the transition section 120, and the second commissure section 113'*c* connects to the second anterior portion 114'. In one example, a separation distance between the first support ring 101 and the central posterior arch 113'*a*, along the central axis 103, is less than a separation distance between the first support ring 101 and any of the first and second commissure sections 113'*b*, 113'*c*. This provides for an improved compression between the first and second support rings 101, 102, along the central posterior arch 113'*a*. The fixation of the annuloplasty device 100 may thus be facilitated. At the same time, the larger separation distance at the first and second commissure sections 113'*b*, 113'*c*, can provide for a more reliable fit to the tissue at the commissure anatomy of the heart valve, e.g. as described above with respect to having the separation distance ($d_1$) at the transition section 120.

In one example, a separation distance between the first commissure section 113'*b* and the first support ring 101 is larger than a separation distance between the second commissure section 113'*c* and the first support ring 101. Hence, as described above with respect to the transition section 120, this provides for an improved fit to the anatomy where the first support ring 101 extends through the commissure and transitions to the second support ring 102 on the opposite side of the heart valve.

A proximal connector element 121 may be fixed to the free end 116 of the first support ring 101. The example in FIG. 1 shows a connector element 121 comprising an aperture for interlocking with a delivery catheter (not shown). Different types of connector elements may be provided at the free end 116. The distal end 116' of the second support ring 102 may be shaped with a blunt tip to reduce the risk of damaging the tissue, see FIG. 1.

The first and/or second support ring 101, 102, may comprise retention units 104, 104', as schematically illustrated in e.g. FIGS. 8 and 11. The first support ring 101 may comprises first retention units 104 and the second support ring 102 may comprise second retention units 104'. The first and second retention units 104, 104', may extend in opposite directions along the axial direction 103'. The retention units 104, 104', are directed towards the valve tissue between the first and second support rings 101, 102, from both of the opposite sides. The first and second retention units 104, 104', may thus produce a retention force on opposite sides of the valve leaflets.

Figure 9:
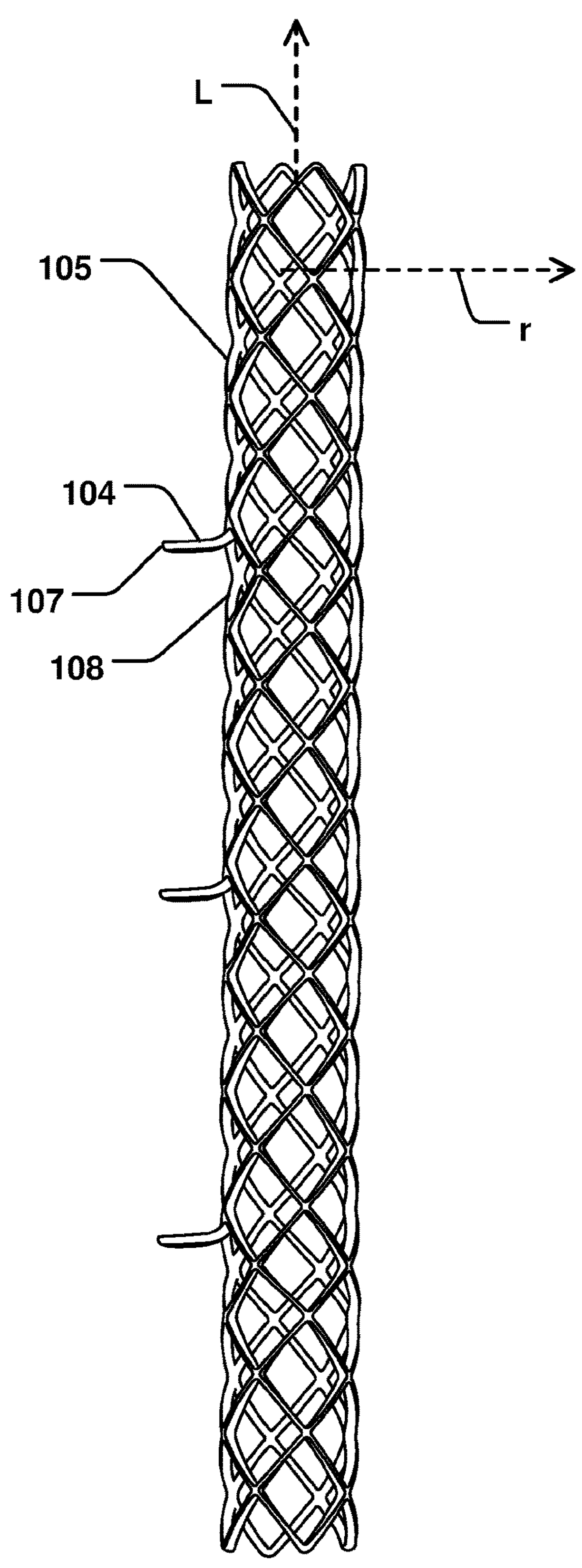
FIG. 9 is a schematic illustration of a stent of an annuloplasty device, in a side view, according to an example.

The annuloplasty device 100 may further comprise a stent 105, 105*a*, 105*b*, arranged around at least a portion of the first and/or second support ring 101, 102. FIG. 8 shows an example where two stents 105*a*, 105*b*, are arranged around portions of the first and second support rings 101, 102. FIG. 9 is a further detailed view of a stent 105 configured to be arranged around at least a portion of the first and/or second support ring 101, 102. It should be understood that the annuloplasty device 100 may comprise a varying number of stents 105 depending on the particular implant site of the annuloplasty device 100. Furthermore, the ratio of the total length of the first and/or second support ring 101, 102, covered by the stent 105, 105*a*, 105*b*, may vary depending on the placement of the annuloplasty device 100. Although reference is made to stent 105 in the present disclosure, it should be understood that any of the stents 105*a*, 105*b*, as exemplified in FIG. 1 may comprise the features as described for stent 105 in relation to FIG. 9. The lattice or framework of the stent 105 may be formed by laser cutting of a tube-shaped material, such as NiTinol or other bio compatible metal alloy and then pushed over the first and/or second support rings 101, 102. The stent 105 thus has a hollow interior to accommodate the first and/or second support rings 101, 102.

The stent comprises retention units 104, 104', as schematically illustrated in FIG. 8 and in the detailed view of FIG. 9. The retention units 104, 104', are shaped to pierce into tissue at the heart valve. The retention units 104, 104', are fixed in relation to the stent 105, and the stent 105 is fixed in relation to the first and/or second support ring 101, 102, on which the stent 105 is arranged. Thus, having stents 105*a*, 105*b*, arranged around at least part of the first and/or second support rings 101, 102, provides for anchoring the annuloplasty device 100 to the valve tissue with the retention units 104, 104'. The first and/or second support rings 101, 102, are thus provided with a robust anchoring mechanism by utilizing a stent 105, 105*a*, 105*b*, as an intermediate fixation structure for the retention units 104, 104', thereby dispensing with the need to attach any retention structures directly to the first and/or second support rings 101, 102. The stent 105 thus provides for increasing the reliability of the anchoring mechanism of the annuloplasty device 100 as the number of separate structures needing to be joined together can be reduced, in particular in the example where the retention units 104, 104', are integrated with the stent 105 as mentioned below. Long-term reliability of the annuloplasty device 100 may thus be improved. The manufacturing of the annuloplasty device 100 may thus also be facilitated, as the number of separate elements is minimized. Manufacturing tolerances may thus be easier to comply with and the overall complexity and associated costs may be reduced, providing for a more viable annuloplasty implant 100. Having an annuloplasty device 100 with stents 105, 105*a*, 105*b*, and associated retention units 104, 104', also provides for a modular annuloplasty device 100 where a core structure of the first and second support rings 101, 102, may be provided with stents 105, 105*a*, 105*b*, having retention units 104, 104', in varying configurations and shapes depending on the particular application. The annuloplasty device 100 may thus be tailored to the particular patient and anatomical circumstances more easily and patient safety can be further improved.

As elucidated above, the retention units 104, 104', may be formed from the material of the stent 105. The retention units 104, 104', may thus be integrated with the stent 105. The detailed view of FIG. 9 is a schematic example of how retention units 104 are formed as a part of the framework of the stent 105. The retention unit 104 may thus be cut as an elongated structure with a free tip 107 within the structural framework of the stent 105. In the example of FIG. 9, the retention unit 104 is surrounded by support elements 108 of the stent 105. The support elements 108 may be arranged in a rhombic pattern or closed cells. The retention units 104 may have a retracted position where the retention units 104 are collapsed to a similar radius as the support elements 108, e.g. by being arranged in the void of individual rhombs or cells at defined positions along the length of the stent 105. As described further below, the retention units 104 may be collapsed when the annuloplasty device 100 is arranged in a delivery catheter (not shown), and subsequently expanded to the expanded state shown in FIGS. 8-9, when removed from the delivery catheter.

In one example, some support elements of the plurality of support elements of a cell may be movable as a retention unit 104, 104', along a radial direction (r), perpendicular to a longitudinal direction (L) of the stent 105. The retention unit 104 illustrated in FIG. 9 may thus be part of the support elements 108 forming a closed cell.

In one example, the retention unit 104, or support element, may be expanded like a bow-like structure in the radial direction (r) to the expanded state. The bow-like shape may thus be configured to apply a pressure into the valve tissue and increase the retention force of the stent 105 at the annulus.

It should be understood the support elements 108 may be cut to form varying patterns. Forming the retention units 104, 104', as integrated structures of the framework of the stent 105 provides for robust and strong retention units 104, 104', and a minimized risk of dislocations or deformations thereof over time. An overall robust and reliable fixation mechanism of the annuloplasty device 100 is thus provided. Manufacturing is also facilitated, as mentioned above, as the number of separate elements of the annuloplasty device 100 requiring assembly is minimized. The retention units 104, 104', may be cut to form various shapes for optimizing the gripping force into the tissue. The retention units 104, 104', may be formed by different cutting techniques such as by laser cutting techniques.

The retention units 104, 104', may be heat-set to assume a defined bent shape as schematically illustrated in the example of FIG. 8, showing an expanded state of the retention units 104. The expanded state may thus correspond to a relaxed state of the retention units 104 where the latter is not acted upon by external forces. The retention unit 104 may be bent and heat-treated during manufacturing so that the retention unit 104 assumes a defined shape in the expanded state. The retention unit 104 may thus have a bias towards the expanded state, by striving towards the relaxed expanded state.

The retention units 104, 104', may thus be resiliently moveable from a retracted state to the expanded state. For example, a force may be applied to the retention unit 104 so that it bends and assumes a retracted position or state, e.g. if a delivery catheter (not shown) applies a compressive force onto the stent 105 and the related retention unit 104. As the stent 105 is ejected from the delivery catheter, when the annuloplasty device 100 is deployed from the delivery catheter, the compressive force is removed and the resilience of the retention unit 104 cause it to move towards the expanded state. This provides for an effective deployment of the retention units 104, 104', as the first and second support rings 101, 102, of the annuloplasty device 100 are ejected from the delivery catheter. The retention units 104, 104', can thus expand and pierce into the valve tissue. The cross-section of the annuloplasty device 100 may be minimized as the retention units 104, 104', may assume the retracted state when positioned inside the delivery catheter. A smaller cross-section provides for a facilitated navigation of the annuloplasty device 100 to a target site in the heart. The delivery catheter may also be subject to less abrasion and wear from the retention units 104, 104', as these may assume the retracted state inside the delivery catheter, causing less friction between the tip 107 and the inside lumen of the delivery catheter. Reduced friction also facilitates moving the annuloplasty device 100 along the delivery catheter, requiring less force and improving the amount of control.

Hence, the retention units 104, 104', may be flexible to bend from the expanded state to the retracted state. This allows also for the retention units 104, 104', to flex to the retracted state if withdrawing the annuloplasty device 100 into a delivery catheter, in case the implantation is aborted or repositioning is needed. The annuloplasty device 100 may thus re-assume the compact cross-sectional profile.

In one example the retention units 104, 104', may comprise a shape-memory material, where activation of the shape-memory material causes the retention units 104, 104', to transfer from the retracted state to the expanded state. For example, the shape-memory material may be temperature activated, so that the retention units 104, 104', move towards the expanded state when subject to heating to the body temperature. This provides for an advantageous deployment of the retention units 104, 104', in some applications.

The retention units 104, 104', may be aligned essentially flush with an outer diameter of the stent 105 in the retracted state. This provides for a compact cross-sectional profile of the annuloplasty device 100 as well as reduced risk of high pressure and abrasion of the retention units 104, 104', against an inner lumen of a delivery catheter.

The stent 105 may be radially contractible along a radial direction (r), perpendicular to a longitudinal direction (L) of the stent 105, so that the stent 105 exerts a force on the first and/or second support ring 101, 102. The radial (r) and longitudinal direction (L) of the stent 105 is schematically indicated in FIG. 9. The stent 105 may thus assume a fixed position in relation to the first and/or second support ring 101, 102, as the force creates friction between the stent 105 and the first and/or second support ring 101, 102. The framework of the stent 105 may thus be cut to allow movement in the radial direction (r), i.e. allowing the support elements 108 of the framework to move in relation to each other, so that the diameter of the stent 105 is variable. The stent 105 may be resiliently expandable in the radial direction (r) so that the stent 105 may be expanded to a radially stretched state. The stent 105 may then strive towards a contracted relaxed state with an inner diameter being less than the inner diameter in the radially stretched state. The inner diameter in the radially stretched state may be more or equal to an outer diameter of first and/or second support ring 101, 102. The stent 105 may thus be positioned over the first and/or second support ring 101, 102, when in the radially stretched state. The stent 105 will thus strive towards the contracted relaxed state with a reduced inner diameter, and accordingly exert the aforementioned force on the first and/or second support ring 101, 102. This provides for a facilitated fixation of the position of the stent 105 in relation to the first and/or second support ring 101, 102. The example in FIG. 8 shows a cover 129 between the stent 105 and the first and/or second support ring 101, 102, as described in more detail below.

The stent 105 may comprise a shape-memory material in one example. Activation of the shape-memory material may cause the stent 105 to contract to a reduced diameter, along the radial direction (r), to apply a force on the first and/or second support ring 101, 102. For example, the shape-memory material may be temperature activated, so that the stent 105 strives towards a reduced inner diameter when subject to heating to the body temperature. This provides for increasing the force exerted on the first and/or second support ring 101, 102, to attain a secure fixation of the stent 105 thereto.

The annuloplasty device 100 may comprise a cover 129 arranged around at least a portion of the first and/or second support ring 101, 102. The cover 129 may be configured to promote endothelialization and the ingrowth of cells over the annuloplasty device 100. For example, the cover 129 may have a surface which is more porous than the surface of the first- and second support rings 101, 102, which promotes the growth of cells over the annuloplasty device 100. The cover 129 may comprise a weave of a textile or a polymer. The stent 105 may be arranged around at least a portion of the cover 106. The cover 129 may in some examples be arranged around the entire length of the first- and second support rings 101, 102.

The stent 105 may exert a force onto the cover 106 so that the cover 129 is pinched between the stent 105 and the first and/or second support ring 101, 102. Having a cover 129 pinched between the stent 105 and the first and/or second support ring 101, 102, provides for attaining a secure fixation of the position of the cover 129 and the stent 105 relative the first and/or second support ring 101, 102. The stent 105 may thus strive towards an inner diameter which is smaller than an outer diameter of the cover 129 when the latter is arranged around the first and/or second support ring 101, 102, so that a force is exerted radially inwards and pinches the cover 129 against the outer surface of the first and/or second support ring 101, 102. In case the stent 105 is formed from a temperature activated shape-memory material, the stent 105 may increase the force radially inwards as the stent 105 is heated to the body temperature, which further increases the strength of the fixation of the stent 105 relative the first and/or second support ring 101, 102.

The first posterior bow 113 may comprise a first posterior stent 105*a* comprising a first plurality of retention units 104, as exemplified in FIG. 8. The second posterior bow 113' may comprise a second posterior stent 105*b* comprising a second plurality of retention units 104' extending in a direction towards the first plurality of retention units 104', as further exemplified in FIG. 8. The first and second pluralities of retention units 104, 104', may thus extend in opposite directions along the axial direction 103'.

Having retention units 104, 104', at both sides along the first and second posterior bows 113, 113', provides for increasing the retention force and the strength by which the annuloplasty device 100 is fixated at the valve. The retention units 104, 104', engage the tissue from both sides of the heart valve, creating a strong retention force in the radial direction, i.e. perpendicular to the axial direction 103'. The first and second supports 101, 102, pinch the tissue from both sides of the valve, so that the retention units 104, 104', a forced into the tissue. The retention units 104, 104', provides for shaping the annulus as desired even with a reduced pinching force, since the retention units 104, 104', provides for fixating the shape of the annulus in the radial direction because of the mentioned retention force. This provides for a more reliable implantation at the heart valve, both in the short term and in the long term.

Having a transition section 120 as described above allows for the retention units 104, 104', of the stent 105, 105*a*, 105*b*, to effectively pierce into the tissue as the first and second support rings 101, 102, accommodate to the anatomy.

Each individual retention unit 104, 104', may engage or pierce into the tissue with a short distance, for a minimum amount of injury to the tissue. The sum of the retention force and friction created from all the retention units 104, 104', still provides for a strong fixation into the tissue. The scar healing will be quick since each individual retention unit 104, 104', as relatively small dimensions. This provides for a non-traumatic and still secure fixation of the annuloplasty device 100. Hence, the retention units 104, 104', may provide for tissue fixation at multiple points across the annuloplasty device 100 resulting in reduced forces per fixation point, and no need for bulky stitching device or knotting device. There is further no risk of coronary artery occlusion or coronary sinus perforation. Hence, the annuloplasty device 100 provides for ease of operation, and a less time consuming procedure than stitching.

In one example, a stent 105 may be further arranged along the first anterior portion 114. This may provide for an advantageous anchoring of the annuloplasty device 100 in some applications. On one example, it is advantageous to have the second anterior portion 114' with a smooth surface free from retention units 114.

In one example the length of the retention units 104, 104', is in the range 0.5-1.5 mm. In another example the length of the retention units 104, 104', is in the range 0.8-1.2 mm, such as 1.0 mm, which may provide for a particularly advantageous fixation into the tissue while being easy to deploy via a delivery catheter.

The retention units 104, 104', may in other examples be integrated with the first and/or second support rings 101, 102. Having retention units 104, 104', integrated with the first and/or second rings 101, 102, may provide for a robust fixation mechanism in some applications.

Figure 10B:
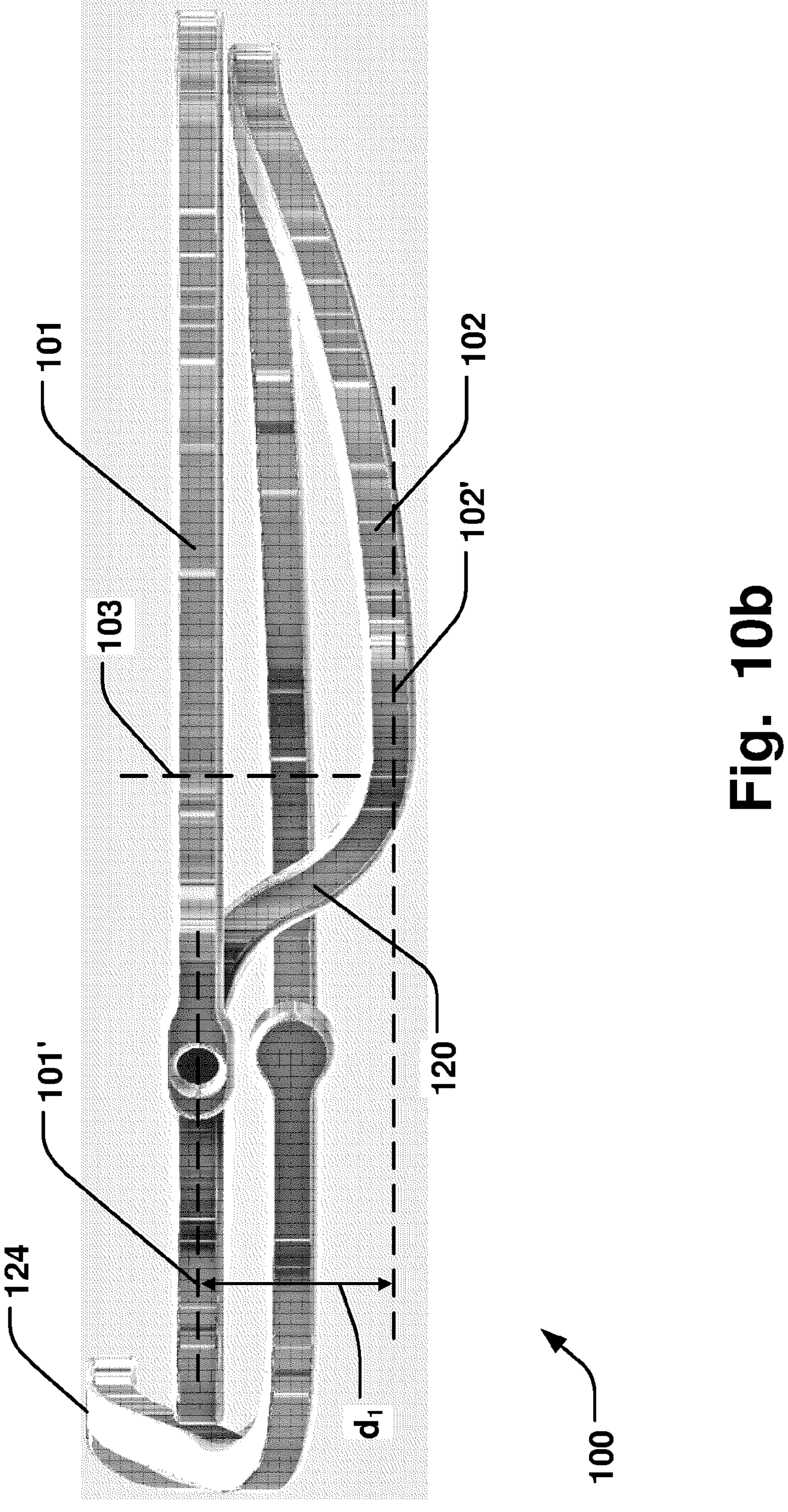
FIG. 10*b* is a schematic illustration of an annuloplasty device, in a side view, according to an example.

In some examples, the first and/or second support rings 101, 102, may have a cross-section which is non-circular, as schematically illustrated in FIGS. 6 and 10*a*-*b*. Having a non-circular shape provides for increasing the compression force between the first and second rings 101, 102, in the coiled configuration while maintaining a compact cross-sectional profile of the first and second rings 101, 102. The dimensions of the sides of the cross-section may be varied in order to provide for an optimized bending resistance of the support rings 101, 102. The cross-section may be essentially rectangular.

The cross-section may vary along a longitudinal direction of the first and/or second support ring 101, 102. The longitudinal direction is the general direction in which the first and/or second support ring 101, 102, extend with an elongated shape. Varying the aforementioned dimensions of the sides (e.g. the sides of a rectangle) along the length of the first and second support rings 101, 102, i.e. along the longitudinal direction, allows for varying the flexibility of the rings 101, 102, along the longitudinal direction and be customized to different anatomical positions around the annulus of the heart valve. This provides for better accommodating movement of the tissue which may be greater at localized sections of the annulus, while other sections may have an increased rigidity for a stronger pinching effect between the first and second support rings 101, 102. A more secure and robust positioning of the device 100 may thus be provided and improved long-term functioning. A varying cross-section provides also for optimizing the flexibility with respect to the delivery and positioning phase of the annuloplasty device 100. E.g. portions of the first and second support rings 101, 102, which are subject to the most bending movement when being inserted in a delivery catheter, such as commissure sections 113'*b*, 113'*c*, (see e.g. FIG. 6) may have a cross-section which increases the flexibility, e.g. by having a reduced area and/or reduced width in the direction in which the support ring 101, 102, is bent. At the same time, the width of the cross-section of the first and/or second support ring 101, 102, may be increased in the direction of the central axis 103 to increase the rigidity and the compression force along the central axis.

Providing a cross-section of the first and second support rings 101, 102, which is non-circular, such as rectangular allows for a facilitated manufacturing of the annuloplasty device 100. For example, the first and second support rings 101, 102, may be cut from a sheet in the form as indicated in FIG. 7. The cut form may then be coiled-up so that the first and second support rings 101, 102, assume a coiled configuration as illustrated in the example of FIG. 6.

Figure 13A:
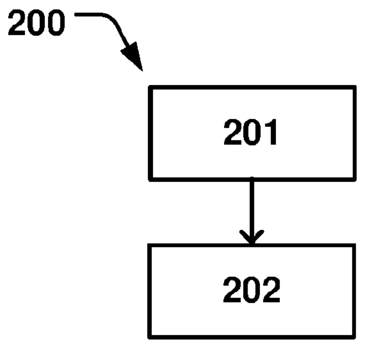
FIG. 13*a* is a flow chart of a method of repairing a defective heart valve, according to an example of the disclosure.

A method 200 of repairing a defective heart valve is disclosed. The method 200 is schematically illustrated in FIG. 13*a*, in conjunction with FIGS. 1-12. The order in which the steps are described should not be construed as limiting, and it is conceivable that the order of the steps may be varied depending on the particular procedure. The method 200 comprises positioning 201 a second support ring 102 of an annuloplasty device 100 on a ventricular side of the heart valve. The method 200 comprises positioning 202 a first support ring 101 of the annuloplasty device 100 on an atrial side of the heart valve. The first and second support rings 101, 102, are arranged as a coil around a central axis 103 on opposite sides of native heart valve leaflets of the heart valve. The first and second support rings 101, 102, are positioned so that the first support ring 101 transitions to the second support ring 102 over a transition section 120 positioned at a commissure 302, 302', of the heart valve leaflets. The first and second support rings 101, 102, extend in respective first and second coil planes 101', 102', being essentially perpendicular to the central axis 103. The transition section 120 bends at least partly along the central axis 103 so that the first coil plane 101' is separated a distance ($d_1$) from the second coil plane 102' along the central axis 103 at the transition section 120. The method 200 provides for the advantageous benefits as discussed above in relation to the annuloplasty device 100 and FIGS. 1-12. The method 200 allows for a facilitated anchoring of the annuloplasty device 100 at the heart valve, due to the improved accommodation to the surrounding anatomy at the heart valve and increased compression force between the first and second support rings 101, 102.

Figure 13B:
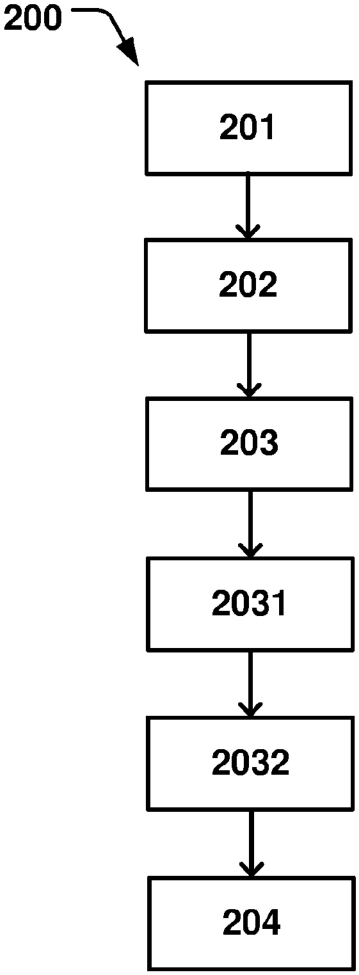
FIG. 13*b* is a flow chart of a method of repairing a defective heart valve, according to an example of the disclosure.

FIG. 13*b* is a further flowchart of a method 200 of repairing a defective heart valve. The method 200 may comprise positioning 203 a stent 105, 105*a*, 105*b*, arranged around at least a portion of the first and/or second support ring, in abutment with valve tissue along said portion so that retention units 104, 104', of the stent are engaged 204 into tissue of the heart valve. The method 200 provides for the advantageous benefits as discussed above in relation to the annuloplasty device 100 and FIGS. 1-10. The method 200 allows for a facilitated anchoring of the annuloplasty device 100 at the heart valve, due to the robust and reliable fixation mechanism provided by stents 105, 105*a*, 105*b*, and the retention units 104, 104', fixed thereto.

The method 200 may comprise positioning 2031 a first posterior stent 105*a* on the atrial side along a first posterior bow 113 of the first support ring 101, and positioning 2032 a second posterior stent 105*b* on the ventricular side along a second posterior bow 113' of the second support ring 102. The method 200 may further comprise positioning an anterior stent (not shown) on the atrial side of the heart valve along a first anterior portion 114 of the first support ring 101.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An annuloplasty device comprising:

A first support ring and a second support ring having a coiled configuration in which the first and second support rings are arranged as a coil around a central axis, the central axis extending in an axial direction from the second support ring to the first support ring, wherein:

the first and second support rings are configured to be arranged on opposite sides of native heart valve leaflets of a heart valve, the first support ring is adapted to be arranged on an atrial side of said heart valve and the second support ring is adapted to be arranged on a ventricular side of the heart valve, the first support ring comprises a first posterior bow and a first anterior portion, the second support ring comprises a second posterior bow and a second anterior portion, the first and second posterior bows are adapted to conform to a posterior aspect of said heart valve and the first and second anterior portions are adapted to conform to an anterior aspect of said heart valve, the first support ring transitions to the second support ring over a transition section adapted to be arranged at a commissure of the heart valve leaflets, the first posterior bow of the first support ring and the second posterior bow of the second support ring extend in respective first and second coil planes being perpendicular to the central axis, the transition section bends at least partly along the central axis so that the first coil plane is separated a distance ($d_1$) from the second coil plane along the central axis at the transition section, a tilted section of the first anterior portion raises above the first posterior bow in the axial direction, the tilted section raises to an apex of maximum separation from the first posterior bow along the axial direction, and the apex directly transitions into the transition section.

2. The annuloplasty device according to claim 1, wherein the tilted section extends in a linear shape from the first posterior bow to the apex.

3. The annuloplasty device according to claim 2, wherein the transition section connects the apex and the second support ring.

4. The annuloplasty device according to claim 2, wherein a separation between the apex and the first posterior bow in the axial direction is less than a separation between the apex and the second posterior bow in the axial direction.

5. The annuloplasty device according to claim 1, wherein the tilted section is movable about the transition section in the axial direction so that the tilted section is movable to extend in parallel with the first and/or second coil plane.

6. The annuloplasty device according to claim 1, wherein:

the second anterior portion comprises an inverted section extending in parallel with the first and second coil planes, and the inverted section and the second posterior bow extend on opposite sides of the first posterior bow with respect to the direction of the central axis.

7. The annuloplasty device according to claim 6, wherein the inverted section raises above the first posterior bow in the axial direction along a width ($w_1$) of the inverted section and said width ($w_1$) is a fraction of a width ($w_2$) of the first or second support ring in a direction in parallel with the first or second anterior portions, where the fraction is in the range 30-80%.

8. The annuloplasty device according to claim 6, wherein a separation ($s_2$) between the apex and the second posterior bow in the axial direction corresponds essentially to a separation ($s_3$) between the inverted section and the second posterior bow in the axial direction.

9. The annuloplasty device according to claim 6, wherein:

the first and second support rings have respective first and second free ends configured to be arranged on opposite sides of the native heart valve leaflets and the inverted section transitions to the free end of the second support ring over an anterior transition section, and the anterior transition section bends at least partly along the central axis so that the free end of the second support ring is arranged on the same side of the first posterior bow as the second posterior bow, with respect to the direction of the central axis.

10. The annuloplasty device according to claim 6, wherein the inverted section is angled from the second coil plane towards the axial direction with a first angle ($v_1$), the transition section is angled from the second coil plane towards the axial direction with a second angle ($v_2$), and the second angle ($v_2$) is an acute angle and is less than the first angle ($v_1$).

11. The annuloplasty device according to claim 1, wherein the first support ring comprises first retention units and the second support ring comprises second retention units, wherein the first and second retention units extend in opposite directions along the axial direction.

12. The annuloplasty device according to claim 1, comprising a stent arranged around at least a portion of the first and/or second support ring, and wherein the stent comprises retention units.

13. The annuloplasty device according to claim 12, wherein the retention units are formed from the material of the stent, whereby the retention units are integrated with the stent.

14. The annuloplasty device according to claim 12, wherein the stent is radially contractible along a radial direction (r), perpendicular to a longitudinal direction (L) of the stent, so that the stent exerts a force on the first and/or second support ring.

15. The annuloplasty device according to claim 12, comprising a cover arranged around at least a portion of the first and/or second support ring, and wherein:

the stent is arranged around at least a portion of the cover, and the stent exerts a force onto the cover so that the cover is pinched between the stent and the first and/or second support ring.

16. The annuloplasty device according to claim 12, wherein:

the stent comprises a first posterior stent comprising a first plurality of retention units and a posterior stent comprising a second plurality of retention units extending in a direction towards the first plurality of retention units, the first posterior bow is arranged within the first posterior stent, and the second posterior bow is arranged within the second posterior stent.

17. The annuloplasty device according to claim 1, wherein at least part of the first anterior portion and/or the second anterior portion is curved to form a respective concave section being concave towards a radial direction (R), the radial direction being perpendicular to the central axis.

18. The annuloplasty device according to claim 1, wherein the first anterior portion is displaced a distance ($I_1$) from the second anterior portion along a radial direction (R) so that at least part of the second anterior portion extends with a greater radius (r) from the central axis than the first anterior portion, the radial direction being perpendicular to the central axis.

19. The annuloplasty device according to claim 1, wherein the first posterior bow is displaced a distance ($I_2$) from the second posterior bow along a radial direction (R), the radial direction being perpendicular to the central axis.

20. The annuloplasty device according to claim 19, wherein at least part of the first posterior bow extends with a greater radius (r) in the radial direction (R) from the central axis than the second posterior bow.

* * * * *